United States Patent
Newman

(10) Patent No.: US 12,383,585 B2
(45) Date of Patent: Aug. 12, 2025

(54) METHODS OF TREATMENT OF INFECTIONS USING BACTERIA

(71) Applicant: Decoy Biosystems, Inc., San Diego, CA (US)

(72) Inventor: Michael J. Newman, San Diego, CA (US)

(73) Assignee: Indaptus Therapeutics, Inc., New York, NY (US)

( * ) Notice: Subject to any disclaimer, the term of this patent is extended or adjusted under 35 U.S.C. 154(b) by 718 days.

(21) Appl. No.: 17/503,032

(22) Filed: Oct. 15, 2021

(65) Prior Publication Data

US 2022/0031768 A1 Feb. 3, 2022

Related U.S. Application Data

(63) Continuation of application No. 16/584,644, filed on Sep. 26, 2019, now Pat. No. 11,147,844.

(60) Provisional application No. 62/737,762, filed on Sep. 27, 2018.

(51) Int. Cl.
| | |
|---|---|
| *A61K 35/74* | (2015.01) |
| *A61K 38/21* | (2006.01) |
| *A61P 31/18* | (2006.01) |
| *A61P 31/20* | (2006.01) |

(52) U.S. Cl.
CPC ............ *A61K 35/74* (2013.01); *A61K 38/212* (2013.01); *A61P 31/18* (2018.01); *A61P 31/20* (2018.01)

(58) Field of Classification Search
CPC .................................................. A61K 35/74
See application file for complete search history.

(56) References Cited

U.S. PATENT DOCUMENTS

| 6,548,287 B1 | 4/2003 | Powell et al. |
| 11,147,844 B2 * | 10/2021 | Newman ............ A61K 39/0275 |
| 2005/0070463 A1 | 3/2005 | Libon et al. |
| 2016/0228523 A1 | 8/2016 | Newman |
| 2017/0348383 A1 | 12/2017 | Coates et al. |
| 2020/0056145 A1 | 2/2020 | Brown et al. |

FOREIGN PATENT DOCUMENTS

| CN | 107184613 A | 9/2017 |
| WO | WO 2005/013980 A1 | 2/2005 |
| WO | WO 2014/107365 A1 | 7/2014 |

OTHER PUBLICATIONS

Healthline (https://www.healthline.com/health/infections, accessed on Sep. 29, 2020; 21 pages (Year: 2020).*
Extended European Search Report and Opinion dated Jun. 3, 2022 for EP Application No. 19866580.4. 13 pages.
Cooperstock, et al. Polymyxin B inactivation of lipopolysaccharide in vaccines of gram-negative bacteria. Infection and Immunity. Jul. 1981; 33(1):315-318.
Vogel, et al. Human macrophage polarization in vitro: Maturation and activationmethods compared. Immunobiology. (2014); 219:695-703.
Castiello, et al. Monocyte-derived DC maturation strategies and related pathways: a transcriptional view. Cancer Immunol Immunother. Apr. 2011 ; 60(4):457-466.
International Search Report and Written Opinion dated Nov. 26, 2019 for PCT/US2019/053289. (9 pages).
Seladi-Schulman. Infections: What you need to know. https://www.healthline.com/health/infections. Healthline. Accessed on Sep. 29, 2020. 21 pages.

* cited by examiner

*Primary Examiner* — Brian Gangle
*Assistant Examiner* — Lakia J Jackson-Tongue
(74) *Attorney, Agent, or Firm* — Sheppard Mullin Richter & Hampton LLP

(57) ABSTRACT

The present disclosure relates generally to compositions, dosage forms, and methods for preventing and treating infections. The compositions include intact and substantially non-viable Gram-negative bacterial cells which have been treated to reduce lipopolysaccharide (LPS)-associated endotoxin activity, which surprisingly have increased activity to trigger immune cell production of cytokines.

8 Claims, 15 Drawing Sheets

Indomethacin

Indomethacin + Entecavir

Indomethacin + Decoy Bacteria

Indomethacin + Decoy Bacteria + Entecavir

METHODS OF TREATMENT OF INFECTIONS USING BACTERIA

CROSS-REFERENCE TO RELATED APPLICATIONS

This application is a continuation of U.S. application Ser. No. 16/584,644, filed Sep. 26, 2019, which claims the benefit under 35 U.S.C. § 119 of U.S. Provisional Application No. 62/737,762, filed Sep. 27, 2018, the contents of which are incorporated herein by reference in their entirety into the present disclosure.

BACKGROUND

For viral infections, such as hepatitis B (HBV) and human immunodeficiency virus (HIV), existing therapy can control viral replication, improve the clinical condition in a majority of treated patients, and result in reduced mortality and morbidity. However, antiviral therapy is hampered by rebounding viremia after cessation of treatment and the emergence of drug resistance mutations. The majority of patients need life-long treatment and a cure of chronic HBV or HIV infection is rarely achieved.

Cytokines and chemokines are known to play an important role in host defense against a wide variety of viral infections, including hepatitis and HIV. Interferon-alpha (IFN-α) is approved for treatment of hepatitis B infection, and several additional cytokines, including interferon-gamma (IFN-γ), interleukin-12 (IL-12), Interleukin-23 (IL-23), GM-CSF and tumor necrosis factor-alpha (TNF-α) have been implicated in host defense against or treatment of viral infections such as hepatitis and HIV.

Preventative vaccination against pathogens requires provision of an antigenic determinant from the pathogen and an adjuvant, which provides immune system danger signals or their down-stream effectors required for activation of an immune response against the pathogen antigen. Therapeutic vaccines intended to treat pre-existing infection, depend on host recognition of pathogen antigenic determinants in the existing infection and also require adjuvants or their down-stream effectors to provide danger signal-mediated immune activation. In some instances, it may be possible to enhance therapeutic vaccines by provision of exogenous pathogen-derived antigens. Immune cells of both the innate and adaptive immune systems use pattern recognition receptors (PRRs) to sense danger in the form of pathogen-associated molecular patterns (PAMPs). The most prominent family of PRRs is comprised of Toll-like receptors (TLRs), found on essentially all immune cells. These receptors (TLRs 1, 2, 3, 4, 5, 6, 7, 8 and 9) respond to products found in many different types of pathogens, including bacteria and viruses. Activation of TLR receptors leads to both direct and indirect activation of immune cell function and immune responses. Direct activation occurs through promotion of cell maturation, proliferation and differentiation, while indirect activation occurs through induction of cytokine and chemokine secretion. A tenth TLR (TLR10) may function as a negative regulatory effector of immune function.

Due to the role of TLRs in host-mediated anti-pathogen immune responses, significant efforts have been made to produce TLR agonist adjuvants and therapeutics for infections. A wide variety of mono-specific, purified or synthetic TLR agonists have been produced and tested in pre-clinical and clinical settings. TLR agonists are used as adjuvants in preventative vaccines. However, although anti-pathogen activity has been observed in the therapeutic vaccine setting, these efforts have encountered significant challenges. Issues encountered have included both lack of potency and excessive toxicity, suggesting that further improvements in preventing and, in particular, treating existing infections with TLR agonists are needed.

SUMMARY

Due to the requirement for activation of both innate and adaptive immune responses for optimal immune defense and the fact that pathogens contain multiple TLR agonist and other danger signal-related constituents, it is contemplated that a multi-TLR agonist therapeutic approach is needed for optimal anti-infective, including anti-viral, therapy. Gram-negative bacteria are known to contain multiple TLR agonists and induce significant TLR agonist-associated immune responses, including cytokine secretion. Wild-type Gram-negative bacteria, which contain high levels of the TLR-4 agonist lipopolysaccharide (LPS) or endotoxin, however, are highly toxic when administered intravenously, largely due to induction of excessive cytokine secretion by immune cells. Gram-negative bacteria also contain agonists for TLRs 1/2, 5 and 9, which can contribute to both immune system stimulation and systemic toxicity.

It is a surprising and unexpected discovery of the present disclosure that treatment of Gram-negative bacteria to reduce its LPS-associated endotoxin activity, e.g., with polymyxin and glutaraldehyde, which can kill the bacteria, keep the bacteria intact, and significantly reduce LPS levels, can at the same time increase the bacteria's ability to induce cytokine secretion from human immune cells. This is unexpected at least because it was assumed that significant reduction of LPS should also lead to a significant reduction in the amount of each of multiple cytokines released by immune cells exposed to the treated bacteria, relative to untreated, wild-type bacteria.

Surprisingly, as shown in Table 1, treated bacteria induced higher levels of 8 out of 9 cytokines secreted by human immune cells, relative to untreated, wild-type bacteria, when tested at the same concentrations of (untreated and treated) bacteria, despite the fact that the treated bacteria had only 4.94% of the LPS level found in untreated bacteria. In addition, despite the significant reduction in LPS, the treated bacteria induced higher levels of cytokines than mono-specific TLR agonists (Table 2). The reduction of LPS-associated endotoxin activity from the treatment, which can be about 75%-99% as measured by an in vitro Limulus Amebocyte Lysate (LAL) assay as compared to untreated, wildtype bacteria, can result in reduction of toxicity. Without being bound by any particular theory, it is contemplated that the intact structure of the treated bacterial cells can help prevent or minimize the release of free LPS into some compartments of the host subject. The results suggest that the treated bacteria may induce a superior immune response than the untreated bacteria or mono-specific agonists, with reduced systemic toxicity, relative to untreated bacteria.

Animal studies further confirmed that such treated bacteria can inhibit both HBV and HIV existing viral infections. Further, when compared to the standard of care (e.g., entecavir for HBV), the treated bacteria exhibited a sustainable and significant inhibitory effect long after cessation of treatment, even though the initial inhibitory effect may take longer to appear. Also interestingly, even though treatments with NSAIDs (e.g., indomethacin) alone did not show observable antiviral effects, combination with an NSAID can synergistically increase the efficacy of the treated bacteria.

Accordingly, in one embodiment, the present disclosure provides a method for treating an infection in a patient in need thereof, comprising administering to the patient an effective amount of a composition comprising a plurality of intact and substantially non-viable Gram-negative bacterial cells which have been treated in such a way as to result in at least 75% reduction of lipopolysaccharide (LPS)-associated endotoxin activity.

In another embodiment, the present disclosure provides a method for preventing infection in a subject in need thereof, comprising administering to the subject an effective amount of a composition comprising a plurality of intact and substantially non-viable Gram-negative bacterial cells which have been treated in such a way as to result in at least 90% reduction of lipopolysaccharide (LPS)-associated endotoxin activity and a pathogen-derived or pathogen-associated antigen.

In one embodiment, the present disclosure provides a method of preventing or treating an infection in a patient in need thereof. The method entails administering to the patient an effective amount of a composition comprising a plurality of intact and substantially non-viable Gram-negative bacterial cells which have been treated in such a way as to result in about 75% to 99% reduction of lipopolysaccharide (LPS)-associated endotoxin activity (active LPS) when measured by the Limulus Amebocyte Lysate (LAL) assay as compared to untreated, wild-type Gram-negative bacterial cells.

In some embodiments, the composition contains about 0.01 to 100 ng active LPS per kg body weight of the patient. In some embodiments, the composition contains about 0.02 to 20 ng active LPS per kg body weight of the patient. In some embodiments, the composition contains about 0.1 to 10 ng active LPS per kg body weight of the patient.

In some embodiments, the composition contains about 2 to 200 ng active LPS per $1\times10^8$ cells. In some embodiments, the composition contains about 10 to 120 ng active LPS per $1\times10^8$ cells. In some embodiments, the composition contains about 20 to 100 ng active LPS per $1\times10^8$ cells.

In some embodiments, the intact and substantially non-viable Gram-negative bacterial cells have been treated in such a way as to result in about 85% to 98% reduction of LPS-associated endotoxin. In some embodiments, the intact and substantially non-viable Gram-negative bacterial cells have been treated in such a way as to result in about 90% to 98% reduction of LPS-associated endotoxin.

In some embodiments, the infection is a viral infection, such as by a virus selected from Table A. In some embodiments, the viral infection is by hepatitis B virus (HBV) or human immunodeficiency virus (HIV).

Also provided, in one embodiment, is a pharmaceutical dosage form comprising a plurality of intact and substantially non-viable Gram-negative bacterial cells which have been treated in such a way as to result in about 75% to 99% reduction of lipopolysaccharide (LPS)-associated endotoxin activity when measured by the Limulus Amebocyte Lysate (LAL) assay as compared to untreated, wild-type Gram-negative bacterial cells, wherein the total LPS-associated endotoxin activity is equivalent to about 0.7 ng to 7000 ng active LPS, preferably equivalent to about 7 ng to 1400 ng active LPS.

In other embodiments, therapeutic compositions, vaccines, and their dosage forms are also described.

DETAILED DESCRIPTION

Figure 1A:
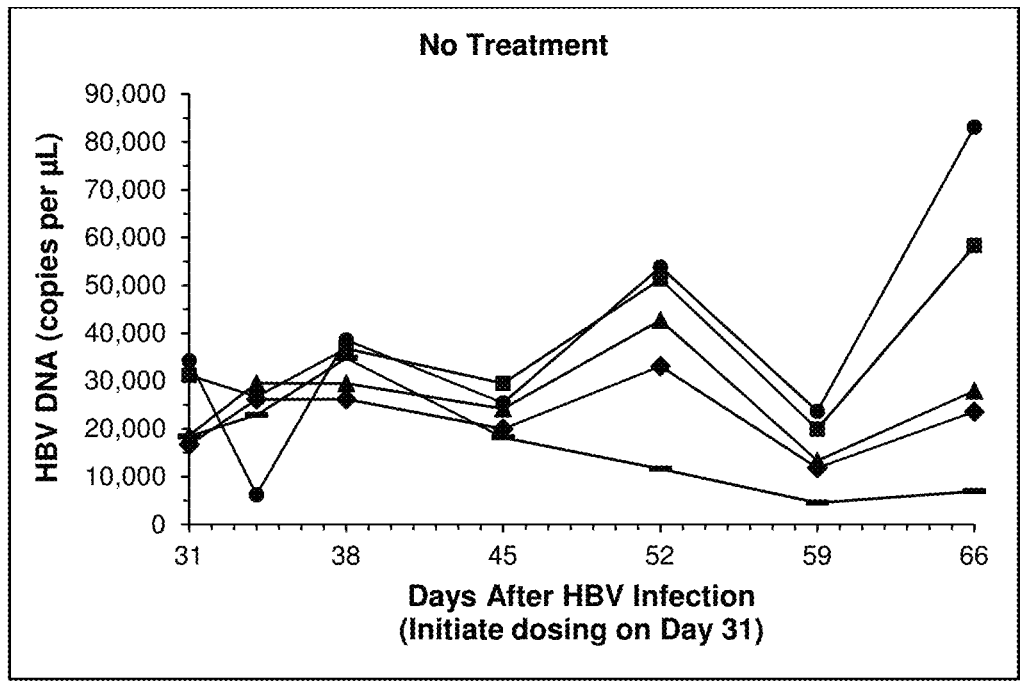
FIG. 1A-1D shows the effects of treatment with Entecavir, treated bacteria (Decoy bacteria), or their combination on the inhibition of HBV DNA production in vivo.

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

Compositions and Methods for Stimulating Immune Response

The experimental examples of the present disclosure demonstrate that intact and non-viable Gram-negative bacterial cells treated to significantly reduce LPS-associated endotoxin activity surprisingly had increased ability to induce cytokine secretion from immune cells. Such treated bacterial cells, therefore, are suitable for providing a safe and effective means to stimulate a subject's immune response. The immune response might be against bacterial, fungal, parasite or viral infections.

In accordance with one embodiment of the present disclosure, therefore, provided is a method of stimulating an immune response in a subject in need thereof. In another embodiment, provided is a method for preventing or treating an infection in a patient in need thereof. In another embodiment, provided is a method for treating immunodeficiency in a patient in need thereof. In another embodiment, a method of vaccinating a subject at risk of infection is provided.

The method, in some embodiments, entails administering to the subject/patient an effective amount of a composition comprising a plurality of treated bacterial cells as disclosed herein. The treated bacterial cells, in some embodiments, are intact and substantially non-viable Gram-negative bacterial cells which have been treated to reduce lipopolysaccharide (LPS)-associated endotoxin activity and/or pyrogenicity.

Candidate bacterial organisms that may be employed by the methods herein are Gram-negative and are derived from those that have LPS-associated endotoxin activity as wild-type organisms. The term "Gram-negative bacteria" refers to bacteria that do not retain the initial basic dye stain (e.g., crystal violet) that is part of the procedure known as the Gram stain. In an exemplary Gram stain, cells are first fixed to a slide by heat and stained with a basic dye (e.g., crystal violet), which is taken up by both Gram-negative and Gram-positive bacteria. The slides are then treated with a mordant (e.g., Gram's iodine), which binds to basic dye (e.g. crystal violet) and traps it in the cell. The cells are then washed with acetone or alcohol, and then counterstained with a second dye of different color (e.g., safranin). Gram-positive organisms retain the initial violet stain, while Gram-negative organisms are decolorized by the wash solvent organic and hence show the counterstain. Exemplary Gram-negative bacteria include, but are not limited to, *Escherichia* spp., *Shigella* spp., *Salmonella* spp., *Campylobacter* spp., *Neisseria* spp., *Haemophilus* spp., *Aeromonas* spp., *Francisella* spp., *Yersinia* spp., *Klebsiella* spp., *Bordetella* spp., *Legionella* spp., Corynebacteria spp., *Citrobacter* spp., *Chlamydia* spp., *Brucella* spp., *Pseudomonas* spp., *Helicobacter* spp. and *Vibrio* spp.

Within gram-negative organisms are the Enterobacteriaceae, a large family that includes, along with many harmless symbionts, many well-known pathogens, such as *Salmonella, E. coli, Yersinia pestis, Klebsiella* and *Shigella, Proteus, Enterobacter, Serratia*, and *Citrobacter*. Members of the Enterobacteriaceae have been referred to as enterobacteria, as several members live in the intestines of animals.

In one embodiment, *E. coli* is selected as the organism. One particular strain contemplated is *E. coli* strain 2617-143-312, (Migula) Castellani and Chalmers (ATCC® 13070™). Additional *E. coli* strains which may be used include MG1655 (ATCC® 47076) and KY8284 (ATCC® 21272).

The Gram-negative organisms used in the methods herein need not be recombinant organisms that contain or express DNA foreign to the wildtype form of the organism. However, in some embodiments, the organisms may be modified to express some non-native molecules, including, for example, pathogen antigens or immune stimulating proteins.

The term "Lipopolysaccharide" (LPS) refers to large molecules consisting of a lipid and a polysaccharide (glycophospholipid) joined by a covalent bond. LPS comprises three parts: 1) O antigen; 2) Core oligosaccharide, and 3) Lipid A. The 0-antigen is a repetitive glycan polymer attached to the core oligosaccharide and comprises the outermost domain of the LPS molecule. Core oligosaccharide attaches directly to lipid A and commonly contains sugars such as heptose and 3-deoxy-D-mannooctulosonic acid (also known as KDO, keto-deoxyoctulosonate). Lipid A is a phosphorylated glucosamine disaccharide linked to multiple fatty acids. The fatty acids anchor the LPS into the bacterial outer membrane, and the rest of the LPS projects from the cell surface.

Endotoxin activity resides in the lipid A domain portion of LPS, and thus is also referred to as "LPS-associated endotoxin activity." When bacterial cells are lysed by the immune system, fragments of membrane containing LPS and lipid A are released into the circulation, causing fever (pyrogenicity), and a potentially fatal shock (called endotoxic or septic shock). Toxicity of LPS is expressed by lipid A through the interaction with cells of the mammalian immune system, a process leading to the secretion of proinflammatory cytokines, including tumor necrosis factor-alpha (TNFα) and interleukin-1beta (IL-1β), which may have fatal consequences for the host.

LPS-associated endotoxin activity can be measured by methods well known in the art, including, for example, the Limulus Amebocyte Lysate (LAL) assay, which utilizes blood from the horseshoe crab, can detect very low levels of LPS. The presence of endotoxin activity will result in coagulation of the limulus blood lysate due to amplification via an enzymatic cascade. Gel clotting, turbidometric, and chromogenic forms of the LAL assay are commercially available.

Enzyme linked immunoadsorbent assay (ELISA)-based endotoxin activity assays are also known such as the EndoLISA® from Hyglos, Munich area of Germany. This assay employs an LPS specific phage protein attached to the solid phase to capture LPS, and following a wash step, the presence of LPS is determined by addition of recombinant Factor C, which when activated by LPS, cleaves a compound that then emits fluorescence. Factor C, present in the Limulus amebocyte lysate, normally exists as a zymogen, and is the primer of the coagulation cascade that occurs in the LAL test.

Pyrogenicity refers to the ability of an agent to cause fever in a subject. Pyrogenicity can be measured as rectal temperature increase in rabbits in response to intravenously administered TLR agonists, organisms or derivatives thereof.

Various methods are available to reduce the endotoxin activity and/or pyrogenicity of Gram-negative organisms. The methods include treatment of the organisms with an agent that binds to LPS or disrupts its formation.

In one embodiment, reduction in endotoxin activity or pyrogenicity is achieved by treating the bacterial organisms with an antibiotic that inactivates endotoxin. A suitable such antibiotic is polymyxin, including polymyxin B or polymyxin E. It is within the skill of one in the art to determine the amount of antibiotic and conditions for treatment. In one embodiment, the polymyxin, either polymyxin B or E, may be employed at a concentration of approximately 3 micrograms to 5,000 micrograms per milliliter. In another embodiment, the concentration of polymyxin may be from about 200 micrograms to 5,000 micrograms per milliliter. In one embodiment, the antibiotic is applied to the bacteria for 10 minutes to 4 hours or from about 30 minutes to about 3 hours.

In one embodiment, the bacteria are grown in the presence of magnesium (Mg) in the form of $MgCl_2$. In one embodiment, the bacteria are treated with polymyxin in the presence of $MgCl_2$, as well as at a temperature suitable to maintain the bacteria's integrity. In one embodiment, the concentration of $MgCl_2$ in the growth medium is from about 0.5 mM to about 5.0 mM, or about 2 mM, and the concentration of $MgCl_2$ in the treatment medium is from about 5.0 mM to about 30 mM, or about 20 mM. In one embodiment, the temperature of the treatment medium is from about 2° C. to about 10° C., or about 4° C. Bacterial integrity is determined by efficiency of recovery in a well-defined pellet after centrifugation at 3,000×g for 10 minutes, and by electron microscopy or optical microscopy with Gram staining. In a preferred embodiment, bacterial recovery after treatment and wash is greater than about 80% and the bacteria appear intact by optical or electron microscopy.

In another embodiment, reduction in endotoxin activity is achieved by treating the bacterial organisms with an antibiotic known to disrupt the biosynthesis of KDO2-Lipid $IV_A$. For example, Goldman et al., J Bacteriol. 170(5):2185-91, 1988 describe antibacterial agents, including antibacterial agent III, which specifically inhibit CTP: CMP-3-deoxy-D-manno-octulosonate cytidylyltransferase activity and which are useful to block the incorporation of 3-deoxy-D-manno-octulosonate (KDO) into LPS of Gram-negative organisms. As LPS synthesis ceased, bacterial growth ceased. The addition of KDO to LPS precursor species lipid $IV_A$ is the major pathway of lipid A-KDO formation in both *S. typhimurium* and *E. coli*. In one embodiment, the antibiotic is antibacterial agent III and Gram-negative bacteria are treated with a suitable amount, such as, for example 5 micrograms per milliliter to 500 micrograms per milliliter for a suitable time, for example 2 to 8 hours.

Likewise, the compound alpha-C-(1,5-anhydro-7-amino-2,7-dideoxy-D-manno-heptopyranosyl)-carboxylate is known to inhibit 3-deoxy-D-manno-octulosonate cytidylytransferase (CMP-KDO synthetase), a cytoplasmic enzyme which activates 3-deoxy-D-manno-octulosonate (KDO) for incorporation into LPS (Nature. 1987 10-16; 329(6135): 162-4). Therefore, treatment of the organisms with the compound can reduce LPS-associated endotoxin activity as well.

In another embodiment, reduction in endotoxin activity is achieved by treating the organisms with an LPS inhibitor. For instance, a bacterial cyclic lipopeptide, surfactin, was shown to bind to lipid A, suppressing its activity (J Antibiot 2006 59(1):35-43).

In addition to LPS-associated endotoxin, various other constituents of Gram-negative organisms can induce or contribute to pyrogenicity and septic shock, including outer membrane proteins, fimbriae, pili, lipopeptides, and lipoproteins (reviewed by Jones, M., Int. J. Pharm. Compd., 5(4):259-263, 2001). Pyrogenicity can be measured by a rabbit method, well known in the art, involving assessment of rectal temperature after intravenous administration of putative pyrogens.

It has been found that treatment of a Gram-negative organism with a combination of polymyxin B and glutaraldehyde produced a 30-fold reduction in pyrogenicity, as measured in rabbits. In one embodiment, 1,000 micrograms per milliliter (µg/mL) of polymyxin B and 1% glutaraldehyde was employed to produce a 30-fold reduction in pyrogenicity, as measured in rabbits. The pyrogenicity is reduced by a combination of polymyxin B reaction with LPS and glutaraldehyde reactivity with LPS and other bacterial constituents. The glutaraldehyde serves a dual role in this setting by also killing the bacteria.

Thus, in one embodiment is provided a method of reducing endotoxin activity and pyrogenicity of and killing a Gram-negative bacterial microorganism by treating said bacteria with a combination of 1,000 µg/mL polymyxin B and 1% glutaraldehyde. In another embodiment, the Gram-negative bacteria are treated with a combination of polymyxin B at a dose range between about 3 µg/mL to about 1,000 µg/mL and glutaraldehyde at a dose range between about 0.1% to about 1.0%. In a further embodiment, the dose range of polymyxin B is between about 100 µg/mL to about 1,000 µg/mL and glutaraldehyde is at a dose range between about 0.5% to about 1.0%. Additionally, Gram-negative bacteria may be treated, for example with a dose range of polymyxin B between about 1,000 µg/mL to about 3,000 µg/mL and glutaraldehyde is at a dose range between about 0.5% to about 1.0%. In another aspect, Gram-negative bacteria maybe treated, for example with a dose range of polymyxin B between about 3,000 µg/mL to about 5,000 µg/mL and glutaraldehyde is at a dose range between about 0.5% to about 2.0%.

In some embodiments, the intact and substantially non-viable Gram-negative bacterial cells have at least about 70% reduction of LPS-associated endotoxin activity (e.g., as measured by the LAL assay) as compared to untreated, wild-type bacteria. In some embodiments, the reduction is at least about 75%, 80%, 85%, 90%, 91%, 92%, 93%, 94%, 95%, 96%, 97%, 98%, 99%, 99.5%, 99.9%, 99.95% or 99.98%. In some embodiments, the reduction is not greater than about 95%, 96%, 97%, 98%, 99%, 99.5%, 99.9%, 99.95%, 99.98% or 99.99%. In some embodiments, the reduction is from about 70% to about 99.99%, from about 80% to about 99.99%, from about 90% to about 99.5% or 99%, from about 91% to about 99%, from about 92% to about 99%, from about 93% to about 97%, from about 94% to about 96%, from about 94.5% to about 95.5%, from about 94% to about 97%, from about 95% to about 98%, from about 96% to about 99%, from about 97% to about 99.5%, or from about 98% to about 99.9%, without limitation.

In some embodiments, certain residual active LPS levels are preferred. For instance, in some embodiments, in a composition of the present disclosure, there is about 1 to 200 ng active LPS per $1 \times 10^8$ cells. In some embodiments, there is about 2 to 200 ng, about 5 to 150 ng, about 5 to 120 ng, about 10 to 120 ng, about 20 to 100 ng, about 20 to 50 ng, about 10 to 50 ng active LPS per $1 \times 10^8$ cells.

In some embodiments, the intact and substantially non-viable Gram-negative bacterial cells have at least about 70% reduction of pyrogenicity (e.g., as measured by in vivo rabbit assay) as compared to untreated wild-type bacteria. In some embodiments, the reduction is at least about 75%, 80%, 85%, 90%, 91%, 92%, 93%, 94%, 95%, 96%, 97%, 98%, 99%, 99.5%, 99.9%, 99.95% or 99.98%. In some embodiments, the reduction is not greater than about 95%, 96%, 97%, 98%, 99%, 99.5%, 99.9%, 99.95%, 99.98% or 99.99%. In some embodiments, the reduction is from about 70% to about 99.99%, from about 80% to about 99.99%, from about 90% to about 99.5% or 99%, from about 91% to about 99%, from about 92% to about 98%, from about 93% to about 97%, from about 94% to about 96%, from about 94.5% to about 95.5%, from about 94% to about 97%, from about 95% to about 98%, from about 96% to about 99%, from about 97% to about 99.5%, or from about 98% to about 99.9%, without limitation.

As provided above, in addition to LPS-associated endotoxin, various other constituents of Gram-negative organisms can also induce or contribute to pyrogenicity, such as outer membrane proteins, fimbriae, pili, lipopeptides, and lipoproteins. In some embodiments, the intact and substantially non-viable Gram-negative bacterial cells are treated in a manner such that the reduction of pyrogenicity is achieved by both reduction of LPS-associated endotoxin activity and reduction of non-LPS-associated pyrogenicity, such as inactivation, removal or blocking of outer membrane proteins, fimbriae, pili, lipopeptides, or lipoproteins. In some embodiments, the reduction of non-LPS-associated pyrogenicity is at least about 50%, 60%, 70%, 75%, 80%, 85%, 90%, 91%, 92%, 93%, 94%, 95%, 96%, 97%, 98%, 99%, 99.5%, 99.9%, 99.95% or 99.98%. In some embodiments, the reduction is not greater than about 60%, 70%, 75%, 80%, 85%, 90%, 91%, 92%, 93%, 94%, 95%, 96%, 97%, 98%, 99%, 99.5%, 99.9%, 99.95%, 99.98% or 99.99%.

Bacteria for administration according to the methods of the disclosure are rendered non-viable or substantially non-viable either prior to administration or become so upon administration. What is meant by "non-viable" is that the organisms are killed by treatment with an exogenous agent, and/or contain a mutation that results in an inability of the organisms to survive in a mammalian host. Substantially non-viable bacteria are strains that have had their viability reduced by at least 80%, 85%, 90%, 95%, 99%, or more.

Bacteria can be made non-viable by treating with a compound such as polymyxin. Polymyxin binds to LPS and interferes with membrane integrity as the bacteria divide, with viability being reduced as a result of permeabilization of the cell envelope. If viability is reduced by this method, steps need be taken to prevent cell lysis and keep the cells intact. Another approach is to grow bacterial strains with conditional mutations in the LPS biosynthesis pathway that are suppressed during growth and then transfer to a non-permissive condition which activates the mutation and disrupts LPS biosynthesis. In each instance, the procedure applied is one that renders the bacteria non-viable by, determining in each setting, the optimal time of treatment or dose of compound, such that viability has been substantially lost with retention of significant bacterial cell integrity. In the case where non-viability is less than 100%, bacteria can be used which contain a mutation preventing further proliferation of viable bacteria in a mammalian host (e.g. a diaminopimelic acid auxotroph, as described by Bukhari and Taylor, J. Bacteriol. 105(3):844-854, 1971 and Curtiss et al., Immunol. Invest. 18(1-4):583-596, 1989).

Diseases and Conditions

The intact and substantially non-viable Gram-negative bacterial cells as disclosed herein are useful for strengthening the immune system of a subject, and thus are useful for preventing or treating diseases and conditions via improved immune response. The intact and substantially non-viable Gram-negative bacterial cells as disclosed herein can also be used as vaccines or immunologic adjuvants for subjects at risk of developing such diseases or conditions.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. The bacterial cells may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal, such as human, dog, cat, cow, sheep, and the like. In one embodiment, the subject is a human.

In some embodiments, the diseases or conditions to be treated are infectious diseases. In some embodiments, the infection is caused by bacteria, fungi, parasites or viruses. In particular, the presently disclosed bacterial cells can be uniquely suitable for treating viral infections, such as those caused by viruses listed in Table A, optionally with a secondary anti-infectious agent.

TABLE A

Listing of viruses

| Virus | Genus, Family |
|---|---|
| Adeno-associated virus | Dependovirus, Parvoviridae |
| Aichi virus | Kobuvirus, Picornaviridae |
| Australian bat lyssavirus | Lyssavirus, Rhabdoviridae |
| BK polyomavirus | Polyomavirus, Polyomaviridae |
| Banna virus | Seadornavirus, Reoviridae |
| Barmah forest virus | Alphavirus, Togaviridae |
| Bunyamwera virus | Orthobunyavirus, Bunyaviridae |
| Bunyavirus La Crosse | Orthobunyavirus, Bunyaviridae |
| Bunyavirus snowshoe hare | Orthobunyavirus, Bunyaviridae |
| Cercopithecine herpesvirus | Lymphocryptovirus, Herpesviridae |
| Chandipura virus | Vesiculovirus, Rhabdoviridae |
| Chikungunya virus | Alphavirus, Togaviridae |
| Cosavirus A | Cosavirus, Picornaviridae |
| Cowpox virus | Orthopoxvirus, Poxviridae |
| Coxsackievirus | Enterovirus, Picornaviridae |
| Crimean-Congo hemorrhagic fever virus | Nairovirus, Bunyaviridae |
| Dengue virus | Flavivirus, Flaviviridae |
| Dhori virus | Thogotovirus, Orthomyxoviridae |
| Dugbe virus | Nairovirus, Bunyaviridae |
| Duvenhage virus | Lyssavirus, Rhabdoviridae |
| Eastern equine encephalitis virus | Alphavirus, Togaviridae |
| Ebolavirus | Ebolavirus, Filoviridae |
| Echovirus | Enterovirus, Picornaviridae |
| Encephalomyocarditis virus | Cardiovirus, Picornaviridae |
| Epstein-Barr virus | Lymphocryptovirus, Herpesviridae |
| European bat lyssavirus | Lyssavirus, Rhabdovirus |
| GB virus C/Hepatitis G virus | Pegivirus, Flaviviridae |
| Hantaan virus | Hantavirus, Bunyaviridae |
| Hendra virus | Henipavirus, paramyxoviridae |
| Hepatitis A virus | Hepatovirus, picornaviridae |
| Hepatitis B virus | Orthohepadnavirus, Hepadnaviridae |
| Hepatitis C virus | Hepacivirus, Flaviviridae |
| Hepatitis E virus | Hepevirus, Unassigned |
| Hepatitis delta virus | Deltavirus, Unassigned |
| Horsepox virus | Orthopoxvirus, Poxviridae |
| Human adenovirus | Mastadenovirus, Adenoviridae |
| Human astrovirus | Mamastrovirus, Astroviridae |
| Human coronavirus | Alphacoronavirus, Coronaviridae |
| Human cytomegalovirus | Cytomegalovirus, Herpesviridae |
| Human enterovirus 68, 70 | Enterovirus, Picornaviridae |
| Human herpesvirus 1 | Simplexvirus, Herpesviridae |
| Human herpesvirus 2 | Simplexvirus, Herpesviridae |
| Human herpesvirus 6 | Roseolovirus, Herpesviridae |
| Human herpesvirus 7 | Roseolovirus, Herpesviridae |
| Human herpesvirus 8 | Rhadinovirus, Herpesviridae |
| Human immunodeficiency virus | Lentivirus, Retroviridae |
| Human papillomavirus 1 | Mupapillomavirus, Papillomaviridae |
| Human papillomavirus 2 | Alphapapillomavirus, Papillomaviridae |
| Human papillomavirus 16, 18 | Alphapapillomavirus, Papillomaviridae |
| Human parainfluenza | Respirovirus, Paramyxoviridae |
| Human parvovirus B19 | Erythrovirus, Parvoviridae |
| Human respiratory syncytial virus | Orthopneumovirus, Pneumoviridae |
| Human rhinovirus | Enterovirus, Picornaviridae |
| Human SARS coronavirus | Betacoronavirus, Coronaviridae |
| Human spumaretrovirus | Spumavirus, Retroviridae |
| Human T-lymphotropic virus | Deltaretrovirus, Retroviridae |
| Human torovirus | Torovirus, Coronaviridae |
| Influenza A virus | Influenzavirus A, Orthomyxoviridae |
| Influenza B virus | Influenzavirus B, Orthomyxoviridae |
| Influenza C virus | Influenzavirus C, Orthomyxoviridae |
| Isfahan virus | Vesiculovirus, Rhabdoviridae |
| JC polyomavirus | Polyomavirus, Polyomaviridae |
| Japanese encephalitis virus | Flavivirus, Flaviviridae |
| Junin arenavirus | Arenavirus, Arenaviridae |
| KI Polyomavirus | Polyomavirus, Polyomaviridae |
| Kunjin virus | Flavivirus, Flaviviridae |
| Lagos bat virus | Lyssavirus, Rhabdoviridae |
| Lake Victoria marburgvirus | Marburgvirus, Filoviridae |
| Langat virus | Flavivirus, Flaviviridae |
| Lassa virus | Arenavirus, Arenaviridae |
| Lordsdale virus | Norovirus, Caliciviridae |
| Louping ill virus | Flavivirus, Flaviviridae |
| Lymphocytic choriomeningitis | Arenavirus, Arenaviridae |

TABLE A-continued

Listing of viruses

| Virus | Genus, Family |
|---|---|
| virus | |
| Machupo virus | Arenavirus, Arenaviridae |
| Mayaro virus | Alphavirus, Togaviridae |
| MERS coronavirus | Betacoronavirus, Coronaviridae |
| Measles virus | Morbilivirus, Paramyxoviridae |
| Mengo encephalomyocarditis virus | Cardiovirus, Picornaviridae |
| Merkel cell polyomavirus | Polyomavirus, Polyomaviridae |
| Mokola virus | Lyssavirus, Rhabdoviridae |
| Molluscum contagiosum virus | Molluscipoxvirus, Poxviridae |
| Monkeypox virus | Orthopoxvirus, Poxviridae |
| Mumps virus | Rubulavirus, Paramyxoviridae |
| Murray valley encephalitis virus | Flavivirus, Flaviviridae |
| New York virus | Hantavirus, Bunyavirus |
| Nipah virus | Henipavirus, Paramyxoviridae |
| Norwalk virus | Norovirus, Caliciviridae |
| O'nyong-nyong virus | Alphavirus, Togaviridae |
| Orf virus | Parapoxvirus, Poxviridae |
| Oropouche virus | Orthobunyavirus, Bunyaviridae |
| Pichinde virus | Arenavirus, Arenaviridae |
| Poliovirus | Enterovirus, Picornaviridae |
| Punta toro phlebovirus | Phlebovirus, Bunyaviridae |
| Puumala virus | Hantavirus, Bunyavirus |
| Rabies virus | Lyssavirus, Rhabdoviridae |
| Rift valley fever virus | Phlebovirus, Bunyaviridae |
| Rosavirus A | Rosavirus, Picornaviridae |
| Ross river virus | Alphavirus, Togaviridae |
| Rotavirus A | Rotavirus, Reoviridae |
| Rotavirus B | Rotavirus, Reoviridae |
| Rotavirus C | Rotavirus, Reoviridae |
| Rubella virus | Rubivirus, Togaviridae |
| Sagiyama virus | Alphavirus, Togaviridae |
| Salivirus A | Salivirus, Picornaviridae |
| Sandfly fever sicilian virus | Phlebovirus, Bunyaviridae |
| Sapporo virus | Sapovirus, Caliciviridae |
| Semliki forest virus | Alphavirus, Togaviridae |
| Seoul virus | Hantavirus, Bunyavirus |
| Simian foamy virus | Spumavirus, Retroviridae |
| Simian virus 5 | Rubulavirus, Paramyxoviridae |
| Sindbis virus | Alphavirus, Togaviridae |
| Southampton virus | Norovirus, Caliciviridae |
| St. louis encephalitis virus | Flavivirus, Flaviviridae |
| Tick-borne powassan virus | Flavivirus, Flaviviridae |
| Torque teno virus | Alphatorquevirus, Anelloviridae |
| Toscana virus | Phlebovirus, Bunyaviridae |
| Uukuniemi virus | Phlebovirus, Bunyaviridae |
| Vaccinia virus | Orthopoxvirus, Poxviridae |
| Varicella-zoster virus | Varicellovirus, Herpesviridae |
| Variola virus | Orthopoxvirus, Poxviridae |
| Venezuelan equine encephalitis virus | Alphavirus, Togaviridae |
| Vesicular stomatitis virus | Vesiculovirus, Rhabdoviridae |
| Western equine encephalitis virus | Alphavirus, Togaviridae |
| WU polyomavirus | Polyomavirus, Polyomaviridae |
| West Nile virus | Flavivirus, Flaviviridae |
| Yaba monkey tumor virus | Orthopoxvirus, Poxviridae |
| Yaba-like disease virus | Orthopoxvirus, Poxviridae |
| Yellow fever virus | Flavivirus, Flaviviridae |
| Zika virus | Flavivirus, Flaviviridae |

In some embodiments, the disease being treated is HBV infection. In some embodiments, the disease being treated in HIV infection.

Dosing and Timing

In some embodiments, the level of LPS-associated endotoxin activity of the intact and substantially non-viable Gram-negative bacterial cells administered to a subject can be determined. In one embodiment, the composition administered contains about 0.01 to 200 ng active LPS per kg body weight of the subject.

The term "active LPS" refers to the LPS in a composition that is able to exhibit LPS-associated endotoxin activity, e.g., as measured by the LAL assay, where 5-9 endotoxin units (EU) are considered to be equivalent to 1 ng of active LPS, based on a standard LPS preparation. The amount of active LPS in a composition can be described as the weight of uninhibited LPS that is able to exhibit the same level of LPS-associated endotoxin activity as the composition.

In some embodiments, the composition (e.g., composition containing the LPS-associated endotoxin activity of the intact and substantially non-viable Gram-negative bacterial cells) administered contains about 0.01 to 150 ng active LPS per kg body weight of the subject. In some embodiments, the composition administered contains about 0.02 to 150 ng, about 0.02 to 100 ng, about 0.05 to 100 ng, about 0.05 to 100 ng, about 0.05 to 50 ng, about 0.05 to 20 ng, about 0.1 to 20 ng, about 0.1 to 10 ng, about 0.1 to 5 ng, about 0.2 to 100 ng, about 0.2 to 50 ng, about 0.2 to 20 ng, about 0.2 to 10 ng, about 0.2 to 5 ng, about 0.3 to 90 ng, about 0.4 to 80 ng, about 0.5 to 70 ng, about 0.6 to 60 ng, about 0.7 to 50 ng, about 0.8 to 40 ng, about 0.9 to 30 ng, about 1 to 20 ng, about 2 to 15 ng, or about 3 to 12 ng active LPS per kg body weight of the subject.

The amount of active LPS administered to a subject may vary depending on the type of the subject and disease. Certain animals, such as mice, rats and dogs, may be able to take advantage of a higher amount (e.g., 250-500-fold as compared to humans and rabbits) of active LPS. In some embodiments, accordingly, the composition administered contains about 10 to 100,000 ng active LPS per kg body weight of the subject. In some embodiments, the composition administered contains about 20 to 50,000 ng, about 30 to 40,000 ng, about 40 to 30,000 ng, about 50 to 20,000 ng, about 0.7 to 10,000 ng, about 80 to 8,000 ng, about 90 to 7,000 ng, about 100 to 6,000 ng, about 200 to 5,000 ng, or about 500 to 5000 ng active LPS per kg body weight of the subject.

The number of bacterial cells administered to a subject can be determined based on the amount of active LPS needed and the endotoxin activity level of the bacterial cells. The number may also depend upon a variety of factors including the age, body weight, general health, sex, diet, time of administration, route of administration, and rate of excretion, drug combination and the severity of the particular disease in the subject undergoing therapy. For example, a dosage may be expressed as a number of bacterial cells described herein per kilogram of the subject's body weight (mg/kg). Dosages of about 10,000 and 100,000,000 cells/kg may be appropriate. In some embodiments, about 100,000 and 10,000,000 cells/kg may be appropriate. In other embodiments a dosage of between 1,000,000 and 5,000,000 cells/kg may be appropriate. Normalization may also be made based on body surface area, expressed in meters squared ($m^2$). In some embodiments, dosages of between about 10,000 and 100,000,000 cells/$m^2$ may be appropriate. In some embodiments, about 100,000 and 10,000,000 cells/$m^2$ may be appropriate. In other embodiments a dosage of between 1,000,000 and 5,000,000 cells/$m^2$ may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The bacterial cells are generally administered after a disease or condition is diagnosed. In some embodiments, the administration starts within 24 hours following the infection, or within 2 days, 3 days, 4 days, 5 days, 6 days or 7 days following the infection. In some embodiments, the administration starts after at least 24 hours following the infection, or after at least 2 days, 3 days, 4 days, 5 days, 6 days or 7 days following the infection. In some embodiments, the administration starts at any time before or after infection and can be carried out as needed.

The administration may also start before an actual infection, or before an infection is diagnosed, as a preventative vaccine or prevention.

Combination Therapies

In one embodiment, the bacterial cells disclosed herein may be used in combination with one or more additional therapeutic agent that are being used and/or developed to treat infections.

In some embodiments, the one or more additional therapeutic agent may be inhibitors of cyclooxygenase (COX) enzymes, such as NSAIDS, including 6MNA, aspirin, carprofen, diclofenac, fenoprofen, flufenamate, flubiprofen, ibuprofen, lndomethacin, ketoprofen, ketorolac, meclofenamate, mefenamic acid, naproxen, niflumic acid, piroxicam, sulindac sulphide, suprofen, tenidap, tolmetin, tomoxiprol, zomepirac, celexocib, etodolac, meloxicam, nimesulide, diisopropyl fluorophosphate, L745,337, NS398, rofecoxib, SC58125, S-aminosalicylic acid, ampyrone, diflunisal, nabumetone, paracetamol, resveratrol, salicin, salicylaldehyde, sodium salicylate, sulfasalazine, sulindac, tamoxifen, ticlopidine, and valeryl salicylate.

In some embodiments, the one or more additional therapeutic agent may be agonists of stimulatory immune checkpoints such as CD27, CD28, CD40, CD122, CD137, OX40, GITR and ICOS, or antagonists of inhibitory immune checkpoints such as A2AR, B7-H3, B7-H4, CTLA-4, IDO, KIR, LAG3, PD-1, PD-L1, TIM-3, and VISTA.

Non-limiting examples of the one or more additional therapeutic agent also include abacavir, acyclovir, adefovir, amantadine, amprenavir, ampligen, arbidol, atazanavir, atripla, balavir, cidofovir, combivir, dolutegravir, darunavir, delavirdine, didanosine, docosanol, edoxudine, efavirenz, emtricitabine, enfuvirtide, entecavir, ecoliever, famciclovir, fomivirsen, fosamprenavir, foscarnet, fosfonet, ganciclovir, ibacitabine, imunovir, idoxuridine, imiquimod, indinavir, inosine, integrase inhibitor, interferon type III, interferon type II, interferon type I, interferon, lamivudine, lopinavir, loviride, maraviroc, moroxydine, methisazone, nelfinavir, nevirapine, nexavir, nitazoxanide, nucleoside analogues, norvir, oseltamivir (Tamiflu®), peginterferon alfa-2a, penciclovir, peramivir, pleconaril, podophyllotoxin, protease inhibitor, raltegravir, ribavirin, rimantadine, ritonavir, pyramidine, saquinavir, sofosbuvir, stavudine, telaprevir, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

In one embodiment, the additional therapeutic agent is interferon alpha.

In some embodiments, the Gram-negative organisms include a polynucleotide that encodes for a non-bacterial protein such as, for example, virus-specific antigens or immune system stimulating proteins. In some embodiments, the Gram-negative organisms include a polynucleotide that encodes for a bacterial antigen, which may be derived from the same or a different bacterial organism, including Gram-positive organisms or other pathogen. As used herein, an antigen is any molecule that can be recognized by an immune response, either an antibody or by an immune cell.

Pharmaceutical Compositions, Dosage Forms and Modes of Administration

Various compositions have been described in the present disclosure that are suitable for the treatment of the diseases or conditions. In one embodiment, provided is a composition or dosage form comprising a plurality of intact and substantially non-viable Gram-negative bacterial cells which have been treated in such a way as to result in about 90% to 99% reduction of lipopolysaccharide (LPS)-associated endotoxin activity when measured by the Limulus Amebocyte Lysate (LAL) assay as compared to untreated wild-type Gram-negative bacterial cells, wherein the total LPS-associated endotoxin activity is equivalent to about 0.7 ng to 7,000 ng active LPS, about 7 ng to 7,000 ng active LPS, about 7 ng to 1400 ng active LPS, or about 70 ng to 1400 ng active LPS.

The compositions can be used as adjuvants or biological response modifiers. As used herein the terms "adjuvant" and "biological response modifier" refer to any substance that enhances an immune response to an antigen. Thus, an adjuvant or biological response modifier is used to stimulate the immune system to respond more vigorously to a foreign antigen or a disease-causing or disease-associated organism. However, in some embodiments, recombinant forms of Gram-negative bacteria that express, e.g., viral proteins or human immune activation proteins such as cytokines or chemokines are contemplated for use in the disclosed methods. In an alternative embodiment, purified immune activation proteins such as cytokines or chemokines are mixed with the Gram-negative organisms prior to administration, or are administered before or after the Gram-negative organisms.

In some embodiments, the intact and substantially non-viable Gram-negative bacterial cells in the dosage form have at least about 70% reduction of LPS-associated endotoxin activity (e.g., as measured by the LAL assay) as compared to untreated wild-type bacteria. In some embodiments, the reduction is at least about 75%, 80%, 85%, 90%, 91%, 92%, 93%, 94%, 95%, 96%, 97%, 98%, 99%, 99.5%, 99.9%, 99.95% or 99.98%. In some embodiments, the reduction is not greater than about 95%, 96%, 97%, 98%, 99%, 99.5%, 99.9%, 99.95%, 99.98% or 99.99%. In some embodiments, the reduction is from about 70% to about 99.99%, from about 80% to about 99.99%, from about 90% to about 99.5% or 99%, from about 91% to about 99%, from about 92% to about 98%, from about 93% to about 97%, from about 94% to about 96%, from about 94.5% to about 95.5%, from about 94% to about 97%, from about 95% to about 98%, from about 96% to about 99%, from about 97% to about 99.5%, or from about 98% to about 99.9%, without limitation.

In some embodiments, the intact and substantially non-viable Gram-negative bacterial cells in the dosage form have at least about 70% reduction of pyrogenicity (e.g., as measured by in vivo rabbit assay) as compared to untreated wild-type bacteria. In some embodiments, the reduction is at least about 75%, 80%, 85%, 90%, 91%, 92%, 93%, 94%, 95%, 96%, 97%, 98%, 99%, 99.5%, 99.9%, 99.95% or 99.98%. In some embodiments, the reduction is not greater than about 95%, 96%, 97%, 98%, 99%, 99.5%, 99.9%, 99.95%, 99.98% or 99.99%. In some embodiments, the reduction is from about 70% to about 99.99%, from about 80% to about 99.99%, from about 90% to about 99.5% or 99%, from about 91% to about 99%, from about 92% to about 98%, from about 93% to about 97%, from about 94% to about 96%, from about 94.5% to about 95.5%, from about 94% to about 97%, from about 95% to about 98%, from about 96% to about 99%, from about 97% to about 99.5%, or from about 98% to about 99.9%, without limitation.

In some embodiments, the reduction of non-LPS-associated pyrogenicity is at least about 50%, 60%, 70%, 75%, 80%, 85%, 90%, 91%, 92%, 93%, 94%, 95%, 96%, 97%, 98%, 99%, 99.5%, 99.9%, 99.95% or 99.98%. In some embodiments, the reduction is not greater than about 60%, 70%, 75%, 80%, 85%, 90%, 91%, 92%, 93%, 94%, 95%, 96%, 97%, 98%, 99%, 99.5%, 99.9%, 99.95%, 99.98% or 99.99%.

In some embodiments, the substantially non-viable bacteria have their viability reduced by at least 80%, 85%, 90%, 95%, 99%, or more.

In some embodiments, the dosage form includes from about 10,000 to about $1\times10^{10}$ such bacterial cells. In some embodiments, the dosage form includes from about 100,000 to about $1\times10^8$ such bacterial cells. In some embodiments, the dosage form includes from about 1000,000 to about $1\times10^7$ such bacterial cells. In some embodiments, the dosage form includes from about $1\times10^6$ to about $1\times10^8$ such bacterial cells.

In some embodiments, the composition further includes a second therapeutic/antiviral agent. In some embodiments, the second therapeutic agent is an NSAID (non-steroidal anti-inflammatory drug). In some embodiments, the second therapeutic agent is a cyclooxygenase inhibitor, preferably selected from the group consisting of 6MNA, aspirin, carprofen, diclofenac, fenoprofen, flufenamate, flubiprofen, ibuprofen, indomethacin, ketoprofen, ketorolac, meclofenamate, mefenamic acid, naproxen, niflumic acid, piroxicam, sulindac sulphide, suprofen, tenidap, tolmetin, tomoxiprol, zomepirac, celexocib, etodolac, meloxicam, nimesulide, diisopropyl fluorophosphate, L745,337, NS398, rofecoxib, SC58125, S-aminosalicylic acid, ampyrone, diflunisal, nabumetone, paracetamol, resveratrol, salicin, salicylaldehyde, sodium salicylate, sulfasalazine, sulindac, tamoxifen, ticlopidine, valeryl salicylate and combinations thereof.

In some embodiments, the second therapeutic agent is an agonist of a stimulatory immune checkpoint preferably selected from the group consisting of CD27, CD28, CD40, CD122, CD137, OX40, GITR and ICOS. In some embodiments, the second therapeutic agent is an antagonist of an inhibitory immune checkpoint preferably selected from the group consisting of A2AR, B7-H3, B7-H4, CTLA-4, IDO, KIR, LAGS, PD-1, PD-L1, TIM-3, and VISTA.

In some embodiments, the second therapeutic agent is selected from the group consisting of abacavir, acyclovir, adefovir, amantadine, amprenavir, ampligen, arbidol, atazanavir, atripla, balavir, cidofovir, combivir, dolutegravir, darunavir, delavirdine, didanosine, docosanol, edoxudine, efavirenz, emtricitabine, enfuvirtide, entecavir, ecoliever, famciclovir, fomivirsen, fosamprenavir, foscarnet, fosfonet, ganciclovir, ibacitabine, imunovir, idoxuridine, imiquimod, indinavir, inosine, integrase inhibitor, interferon type III, interferon type II, interferon type I, interferon, lamivudine, lopinavir, loviride, maraviroc, moroxydine, methisazone, nelfinavir, nevirapine, nexavir, nitazoxanide, nucleoside analogues, norvir, oseltamivir (Tamiflu®), peginterferon alfa-2a, penciclovir, peramivir, pleconaril, podophyllotoxin, protease inhibitor, raltegravir, ribavirin, rimantadine, ritonavir, pyramidine, saquinavir, sofosbuvir, stavudine, telaprevir, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, zidovudine and combinations thereof.

In some embodiments, the second therapeutic agent is interferon alpha.

Compositions described herein may be formulated in a variety of ways for use in the methods described herein. In one embodiment, the composition comprises the organisms as described throughout and a pharmaceutically acceptable carrier.

"Pharmaceutically acceptable carriers" refers to any diluents, excipients, or carriers that may be used in the compositions. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as magnesium sulfate, protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, cryopreservatives such as trehalose and mannitol and wool fat. Suitable pharmaceutical carriers are described in Remington's Pharmaceutical Sciences, Mack Publishing Company, a standard reference text in this field.

The compositions are formulated for pharmaceutical administration to a mammal, preferably a human being. Such pharmaceutical compositions of the invention may be administered in a variety of ways, including parenterally. The term "parenteral" as used herein includes subcutaneous, intravenous, intramuscular, intra-articular, intra-synovial, intrasternal, intrathecal, intrahepatic, intralesional and intracranial injection or infusion techniques.

Sterile injectable forms of the compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compositions may be formulated for parenteral administration by injection such as by bolus injection or continuous infusion.

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, or subcutaneously.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Some examples of suitable excipients include lactose, dextrose, sucrose, sorbitol, mannitol, trehalose, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1. Pre-Clinical Efficacy Characterization of a Systemically Administered Multiple Toll-Like Receptor (TLR) Agonist This example tested the hypothesis that significant reduction without complete elimination of LPS activity, in conjunction with killing and stabilization of non-pathogenic, Gram-negative bacteria may produce a multiple TLR product that can safely and effectively induce anti-tumor immune responses via i.v. administration.

Non-pathogenic, Gram-negative E. coli were treated with polymyxin B and glutaraldehyde under conditions to kill and stabilize the cells, producing >90% reduction in LPS endotoxin activity and pyrogenicity ("treated bacteria," also referred to as "Decoy bacteria" or simply "Decoy"). Endotoxin activity and pyrogenicity were quantified using Limulus amebocyte lysate and in vivo rabbit assays. Bacterial integrity was assessed by electron and light microscopy. Antitumor activity was determined using standard syngeneic and xenograft tumor models.

Treated bacteria exhibited a 3-fold reduction in acute in vivo toxicity relative to untreated bacteria. Surprisingly, induction of anti-tumor cytokine secretion by murine and human peripheral blood mononuclear cells (PBMCs) was not compromised, relative to untreated bacteria. Treatment with the treated bacteria (i.v.) produced significant single agent anti-tumor activity against orthotopic murine colorectal carcinoma and metastatic murine pancreatic carcinoma.

Synergistic combination activity, including eradication of established tumors, with a therapeutic index of up to 10-fold, was observed in combination with IL-2 or low-dose cyclophosphamide (LDC) in murine colorectal carcinoma models, with LDC in a subcutaneous (s.c.), murine non-Hodgkin's lymphoma (NHL) model and with LDC plus rituximab in a s.c., human NHL model. Synergistic anti-tumor activity was also observed in combination with a low-dose, non-steroidal anti-inflammatory drug (NSAID) in a metastatic, murine pancreatic carcinoma model. In addition, tumor eradications were observed in combination with NSAID and were enhanced by addition of anti-PD1 therapy in a s.c., murine hepatocellular carcinoma model. Optimal (80-100%) tumor eradication was shown to be mediated by natural killer (NK), CD4+ and CD8+ T cells. Immunological memory (80-100% and partial), determined by rejection of subsequent tumor challenge, was demonstrated in both immune competent and innate only settings, respectively.

Example 2. Induction of Cytokine Secretion by Treated Bacteria

This example examined the ability of the treated bacteria in inducing cytokine secretion from human peripheral blood mononuclear cells.

Non-pathogenic, Gram-negative E. coli were treated with polymyxin B and glutaraldehyde under conditions to kill and stabilize the cells, producing >90% reduction in LPS endotoxin activity and pyrogenicity ("treated bacteria," "Decoy bacteria," or simply "Decoy") see Example 1 and U.S. Pat. No. 9,265,804 B2). Endotoxin activity and pyrogenicity were quantified using Limulus amebocyte lysate and in vivo rabbit assays. Bacterial integrity was assessed by light microscopy after Gram-staining.

Ten-fold increments of $1\times10$ to $1\times10^8$ untreated or treated bacteria were incubated with $2.5\times10^5$ human peripheral blood mononuclear cells (PBMCs) in RPMI culture medium containing 2.5 mM glutamine, 10% human serum and 1% penicillin and streptomycin at 37° C. with 5% $CO_2$ for 48 hours. Supernatants were harvested by centrifuging plates at 1,000 rpm for 10 minutes and stored at −80° C. Luminex analysis of cytokine levels was carried out with Millipore Human Cytokine/Chemokine Magnetic Bead panels HCY-TOMAG-60K and HSTCMAG-28SK. Levels of cytokines were interpolated off a standard curve using a 5-point non-linear regression analysis where the fit=$(A+((B-A)/(1+(((B-E)/(E-A))*((x/C)^D)))))$. The interpolated data was normalized to vehicle control or unstimulated control and analyzed. PBMCs from fresh normal peripheral blood leukapheresis paks (ALLCells, Alameda, CA) were isolated using a Ficoll gradient (Ficoll-Paque PLUS, Cat #17-144-02, density 1.077+/−0.001 g/mL from GE Healthcare Bio-Sciences, Pittsburgh, PA). The bacteria vehicle was phosphate-buffered saline (PBS) with no calcium and 2 mM $MgCl_2$.

Results presented are the peak levels determined for each cytokine using the same untreated or treated bacterial dose. The treated bacteria contained 4.94% as much LPS as the untreated bacteria on a per bacterium basis, as measured by the in vitro Limulus amebocyte lysate (LAL) assay.

TABLE 1

Level of Cytokines from PBMC Induced by Treated Bacteria

| Secretion by Human PBMCs In Vitro | Untreated Bacteria | Treated Bacteria |
|---|---|---|
| Cytokine | 48-hour pg/mL peak (mean of triplicates) at same bacteria dose for each cytokine | |
| GM-CSF | 1,094 | 1,197 |
| IFNγ | 175,866 | 47,488* |
| IL-1β | 11,976 | 17,651 |
| IL-6 | 78,422 | 98,534 |

TABLE 1-continued

Level of Cytokines from PBMC Induced by Treated Bacteria

| Secretion by Human PBMCs In Vitro | Untreated Bacteria | Treated Bacteria |
|---|---|---|
| IL-8 | 126,942 | 166,769 |
| IL-10 | 6,970 | 7,670 |
| IL-12p70 | 176 | 528 |
| IL-23 | 0 | 119 |
| TNFα | 49,782 | 77,919 |

*Results presented are the peak levels determined for each cytokine, which occurred at the same untreated and treated bacterial dose, except for IFNγ, which peaked at a lower dose for the untreated bacteria and was compared to the same dose of treated bacteria.

The activities of the treated bacteria were compared to a few toll-like receptor agonists (TLRa) and isolated LPS. The experiment was carried out as described for Table 1. Toll-like receptor agonists (TLRa) were obtained from Invivo-Gen (San Diego, CA) and titrated in the experiment as follows; CpG ODN 2006 (#tlrl-2006, 0.005 to 5 micromolar), Poly(I:C) (#tlrl-pic, 0.001 to 100 microgram/mL), R848 (#tlrl-r848, 0.1 to 100 microgram/mL) and E. coli LPS (#tlrl-pb5lps, 10 to $1 \times 10^6$ picogram/mL). TLR agonist stocks were prepared as recommended by the manufacturer at up to their recommended limits of solubility and results are the peak cytokine levels determined for each TLRa and the treated bacteria. The results are presented in Table 2 below.

TABLE 2

Induction of Cytokine as Compared to Individual TLR Agonists

| Cytokine | CpG ODN (TLR9a) | Poly(I:C) (TLR3a) | R848 (TLR 7/8a) | LPS (TLR4a) | Treated Bacteria |
|---|---|---|---|---|---|
| | pg/mL (full titration peak mean) | | | | |
| GM-CSF | 0 | 0 | 87 | 175 | 1,197 |
| IFNγ | 7 | 103 | 31,324 | 29,416 | 91,475 |
| IL-1β | 1 | 22 | 9,990 | 4,631 | 17,651 |
| IL-6 | 241 | 129 | 40,555 | 54,174 | 98,534 |
| IL-8 | 2,436 | 1,452 | 116,135 | 143,459 | 166,769 |
| IL-10 | 374 | 8 | 940 | 3,542 | 7,670 |
| IL-12p70 | 4 | 18 | 253 | 109 | 528 |
| TNFα | 51 | 208 | 33,393 | 24,944 | 77,919 |

Example 3. Animal Testing of Treating Viral Infection with the Treated Bacteria

This example tests the treated bacteria, which can be prepared as shown in Examples 1 and 2, for their activity in treating viral infections in animals.

Animal models of hepatitis B (HBV) infection employed in this example can be any one of the following, the hydrodynamic injection model, FVB/N model, adeno virus delivery model, adeno-associated virus model, Woodchuck hepatitis virus infection model, chimpanzee model, Tupaia model, HBV transgenic mouse model, HBV-Trimera model and human liver-chimeric model. Suitable HIV animal models can also be used to test the activity of the treated bacteria in preventing or treating HIV infection.

Formulations of treated bacteria, with a total amount of LPS activity as measured by in vitro Limulus amebocyte lysate (LAL) assay in different ranges, are administered to animals infected by a virus or expressing viral genes. In some animals, additional immune-stimulating or antiviral agents will be used as a combination therapy. Animals not receiving the treatments and animals treated with other immune-stimulating or antiviral agents are used as control. It is contemplated that the treated bacteria exhibit effective antiviral activities in these animal models.

Example 4. HBV Inhibition in Mice

Adeno-associated virus/hepatitis B virus (AAV/HBV) is a recombinant AAV carrying replicable human HBV genome. Taking the advantage of the highly hepatotropic feature of genotype 8 AAV, the human HBV genome can be efficiently delivered to mouse liver cells. Infection of immune competent mice with AAV/HBV can result in long term HBV viremia, including release of human HBV virions, HBsAg and HBeAg into the blood, which mimics chronic HBV infection in patients. The AAV/HBV model can be used to evaluate the in vivo activity of various types of anti-HBV agents. Furthermore, this is an appropriate model for evaluation of immune modulators (see, for example Huang et al., Int. J. Onc. v39 pp1511-1519, 2011).

rAAV8-1.3HBV, genotype D, was purchased from Beijing FivePlus Molecular Medicine Institute (batch number A2018092406). The stock virus of $1 \times 10^{12}$ viral genome (v.g.)/mL was diluted to $5 \times 10^{11}$ v.g./mL with sterile phosphate-buffered saline (PBS) and $1 \times 10^{11}$ v.g. AAV/HBV in 200 μL was injected per 5 week old male C57BL/6 mouse 31 days prior to the initiation of dosing (day −31).

Blood samples (~100 μL) were collected into K2-EDTA coated tubes via submandibular bleeding on days −17, −7 and −4. The samples were centrifuged at 7,000 g (4° C.) for 10 minutes for plasma collection. At least 40 μL plasma samples were prepared to determine the level of HBV-DNA by qPCR, and the levels of HBs Antigen (HBsAg) and HBe Antigen (HBeAg) by enzyme-linked immunosorbent assay (ELISA). Remaining plasma samples were stored at −80° C. for post-life assays. Based on the plasma levels of HBV DNA, HBsAg, HBeAg and body weights on days −17, −7 and −4, mice with qualified viral infection levels were selected and randomly divided into 7 groups with 5 mice in each group on day −1. All mice were evenly distributed in each group, to ensure no significant difference existed between each group in terms of HBV DNA, HBsAg, HBeAg level and body weight on day −4.

Decoy bacteria were prepared as described in Example 1 and U.S. Pat. No. 9,265,804 B2, with an LPS-endotoxin activity range of approximately 2,000 to 6,000 endotoxin units (EU) or approximately 250 to 750 ng LPS per $10^9$ killed bacterial cells. Animal groups were untreated, treated with Entecavir (ETV) at 0.005 mg/kg orally (p.o.) daily on days 0-34, Decoy at $2 \times 10^8$ killed bacteria per mouse administered tail vein i.v. on days 1, 2, 8, 9, 15, 16, 22, 23, 29 and 30, or ETV and Decoy. Plasma samples were obtained weekly an analyzed for HBV-DNA, HBsAg and HBeAg as described above. Levels of HBV DNA (copies), HBsAg and HBeAg in mice from the treated groups were compared to the levels in the no treatment group at each comparable time-point by unpaired, non-parametric Mann-Whitney statistical analysis.

Figure 1B:
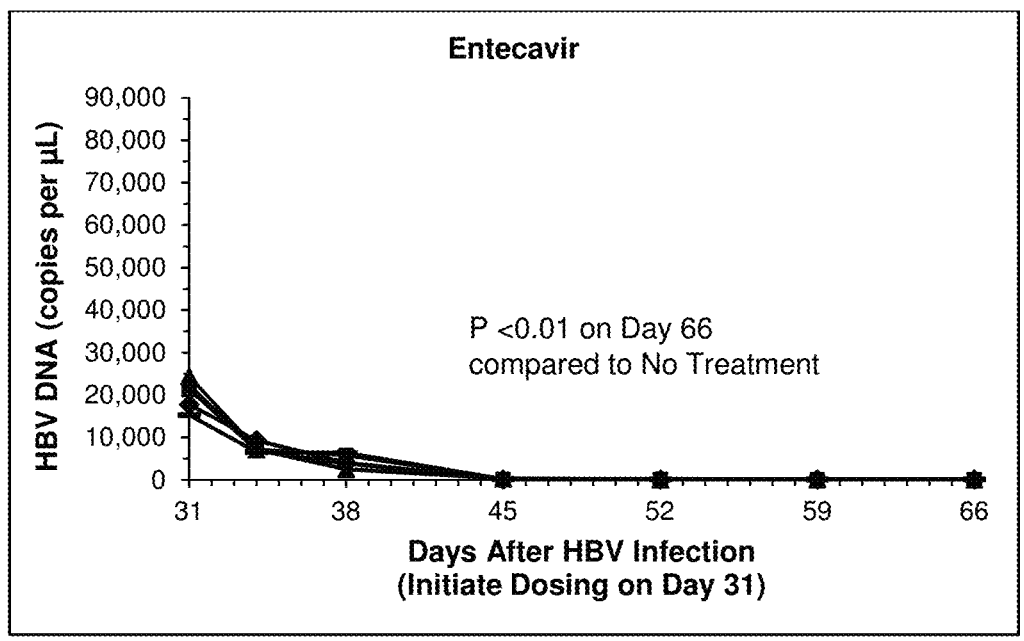
Figure 1C:
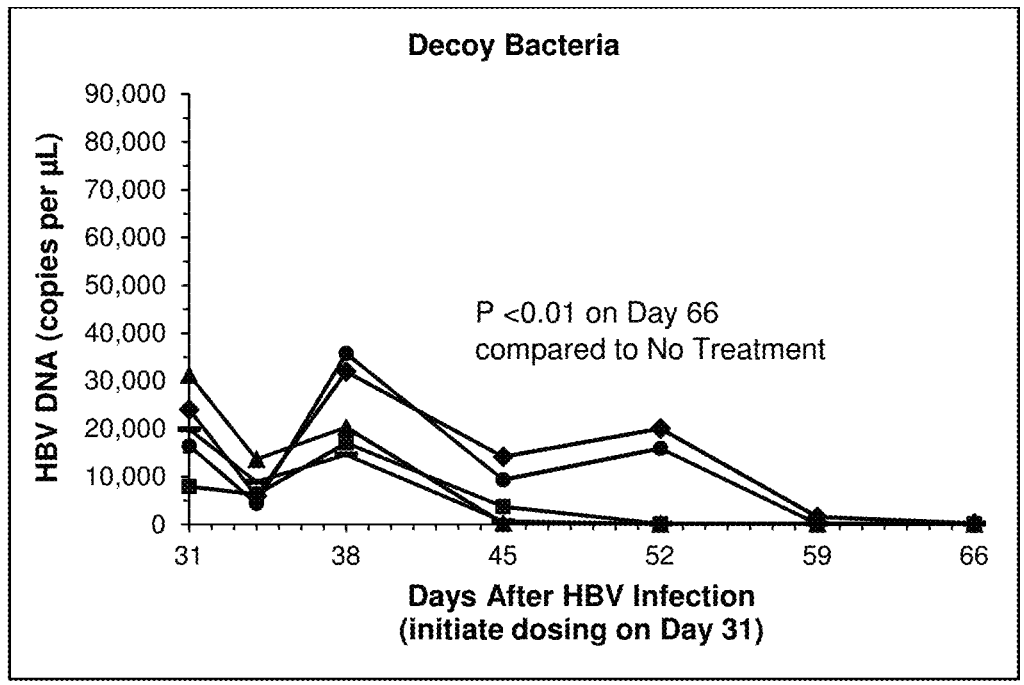
Figure 1D:
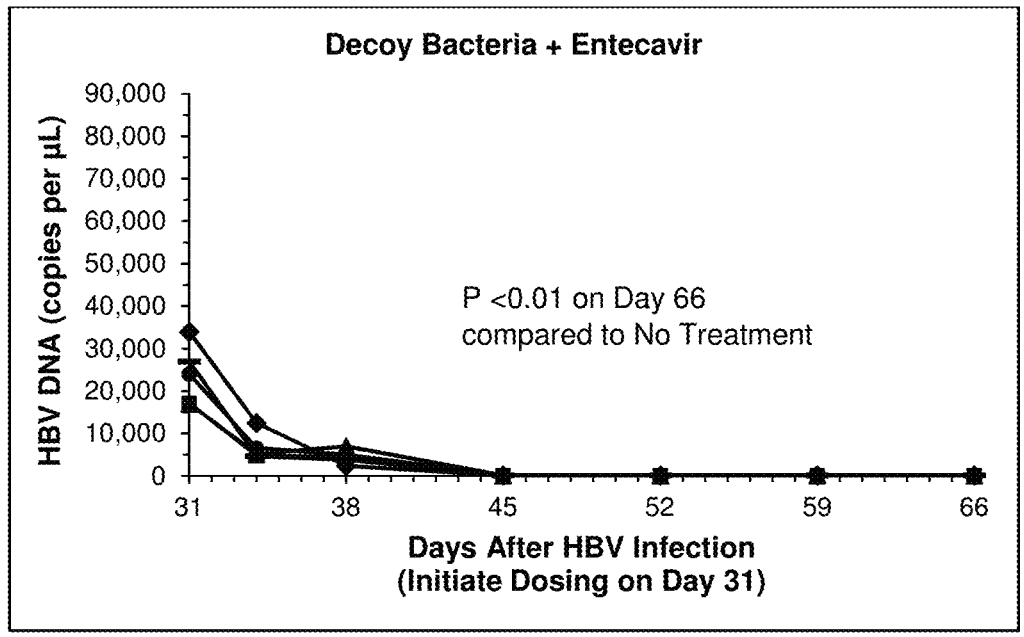

FIG. 1 demonstrates that the standard of care therapy (ETV) significantly inhibited HBV DNA production within 3 days of initiation of dosing, bringing the plasma level in 5/5 mice down to the lower limit of quantitation (120 copies/μL plasma) by day 28 of daily dosing (day 59 after infection) (FIG. 1B). Decoy also significantly inhibited HBV DNA production, bringing the plasma level in 3/5 mice down to the lower limit of quantitation by day 28 of twice weekly dosing (day 59 after infection) (FIG. 1C). Inhibition of HBV DNA by ETV+Decoy was similar to ETV alone, demonstrating that there was no antagonistic interaction up to this point in compound administration (FIG. 1D).

Figure 2:
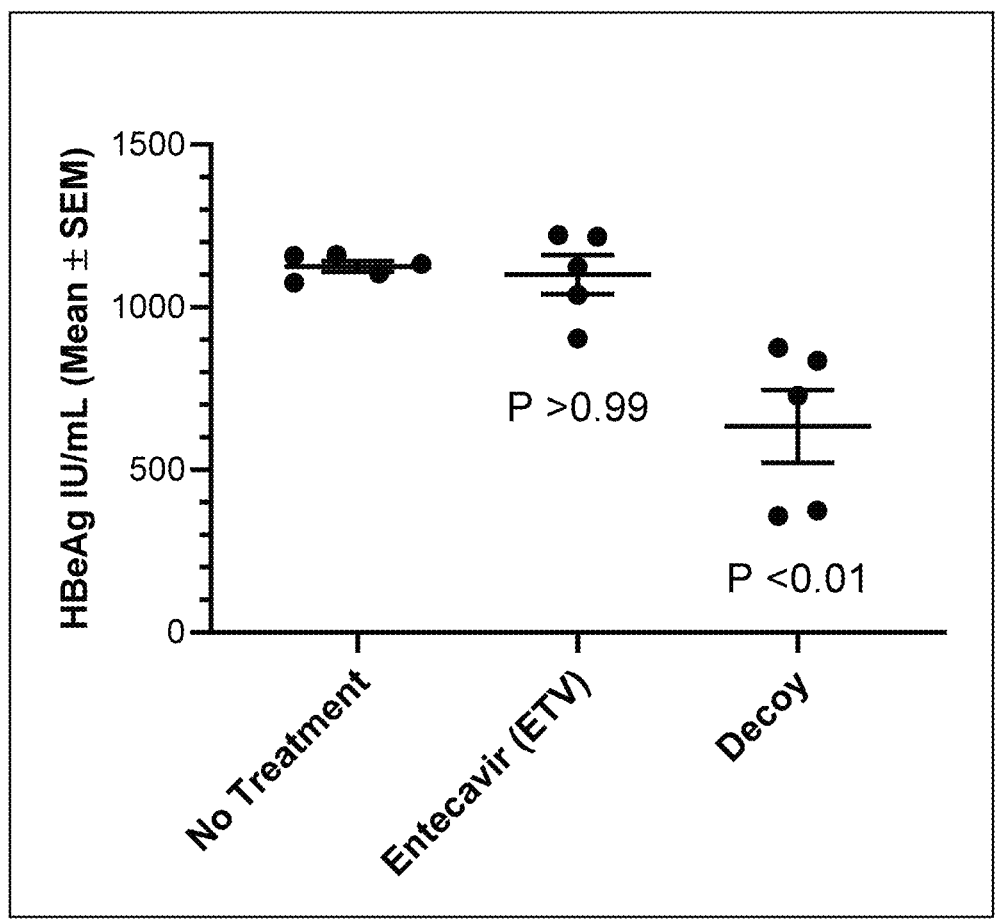
FIG. 2 shows that Decoy bacteria, but not Entecavir, decreased HBeAg levels in vivo.

No inhibition of HBsAg or HBeAg production was observed with ETV. However, Decoy was found to inhibit production of HBeAg on day 28 of dosing (Day 59 after infection) (FIG. 2).

This example therefore demonstrates that, as with the standard of care (ETV), Decoy bacteria can also significantly inhibit HBV replication, although Decoy bacteria took longer to exhibit inhibitory activity, which is consistent with an immunological basis for the Decoy mechanism of action. However, unlike ETV which only inhibited HBV DNA production, Decoy bacteria have the advantage of inhibiting the production of the HBe antigen as well.

Example 5. Long-Term HBV Inhibition

This experiment was conducted in order to determine if a non-steroidal anti-inflammatory drug (NSAID) could enhance anti-viral activity by Decoy bacteria, if the anti-viral activity of Decoy is lost after cessation of treatment, and the potential toxic effects of ETV, Decoy and ETV+Decoy treatment. The experiment was carried out as described in Example 4, except that the AAV/HBV virus was injected at day −29, relative to start of dosing. HBV-DNA, HBsAg and HBeAg levels in plasma were determined on days −15, −8 and −1, relative to start of dosing on day 0, and the ETV dose was increased to 0.1 mg/kg. In addition, all groups represented in FIGS. 3, 4, 5 and 6 were administered indomethacin (NSAID) daily (10 µg/mL in drinking water). Dosing was carried out for 5 weeks as in Example 4, with plasma levels of HBV-DNA, HBsAg and HBeAg determined weekly, as well as every other week for 27 weeks after cessation of treatment. Inhibitory activity was determined by comparing treated groups at each time point to the control (indomethacin alone) group at the same time-point by unpaired, non-parametric Mann-Whitney statistical analysis.

Upon termination, the liver from each mouse was divided into multiple sections, snap frozen in liquid nitrogen immediately upon collection and stored at −80° C. Liver sections were used for HBV DNA detection and additional sections from each mouse liver were fixed in 10% neutral buffered formalin (NB F) for about 24 hours, then transferred for routine dehydration and paraffin embedding. Paraffin blocks were sectioned for hematoxylin-eosin (H&E) staining and pathology analysis, as well immunohistochemistry (IHC) analysis for HBsAg and HBcAg.

Figure 3A:
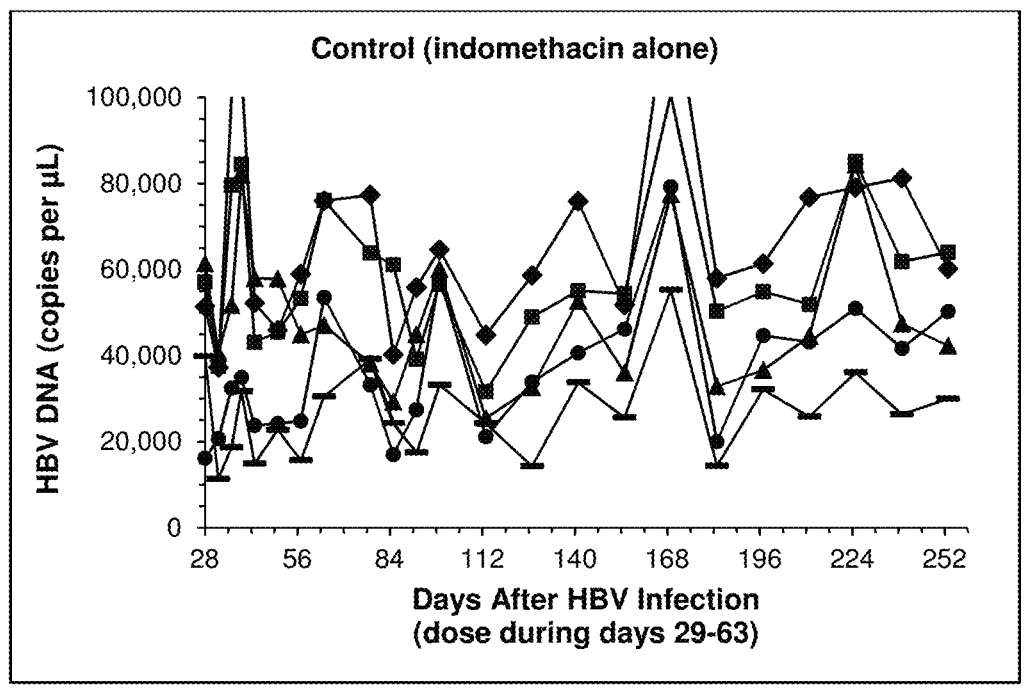
FIG. 3A-D show the results of a longer-term study of the inhibition of HBV DNA production in vivo.
Figure 3B:
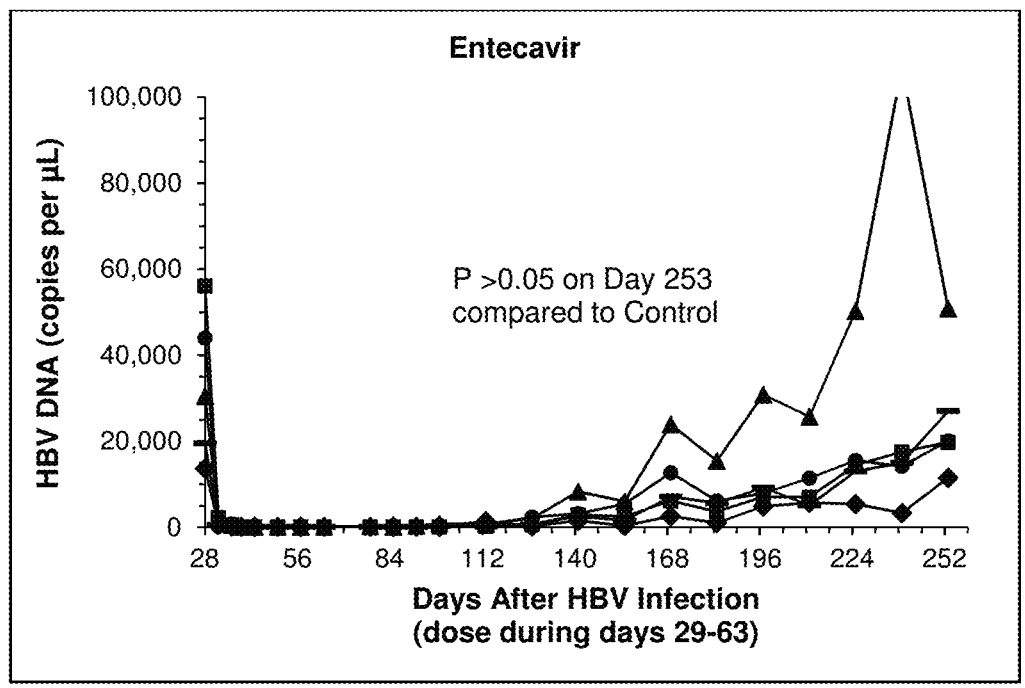
Figure 3C:
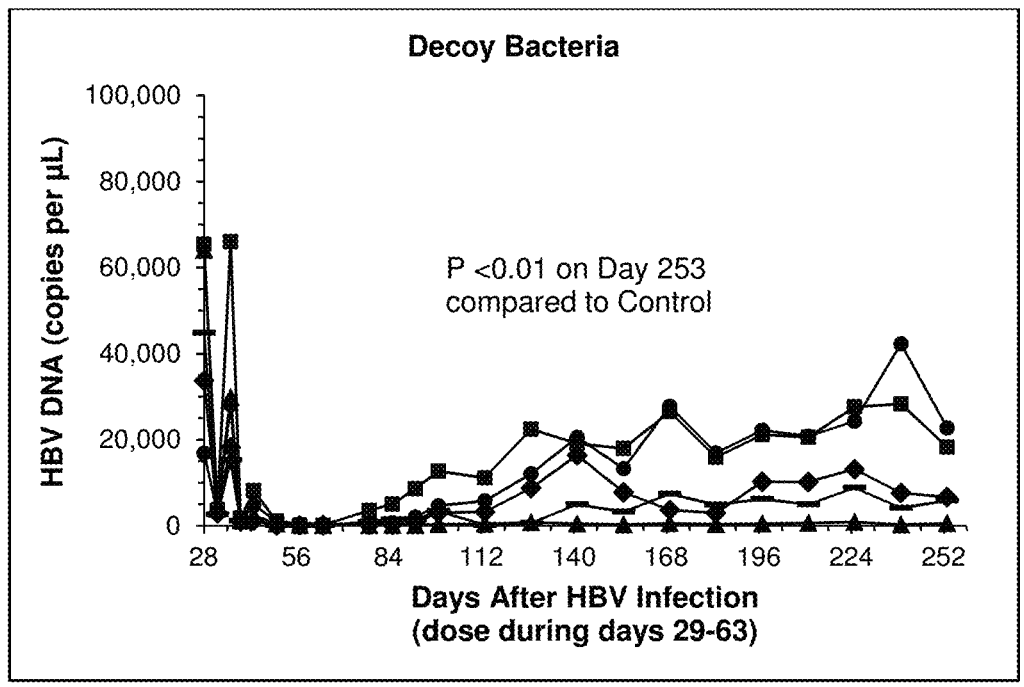
Figure 3D:
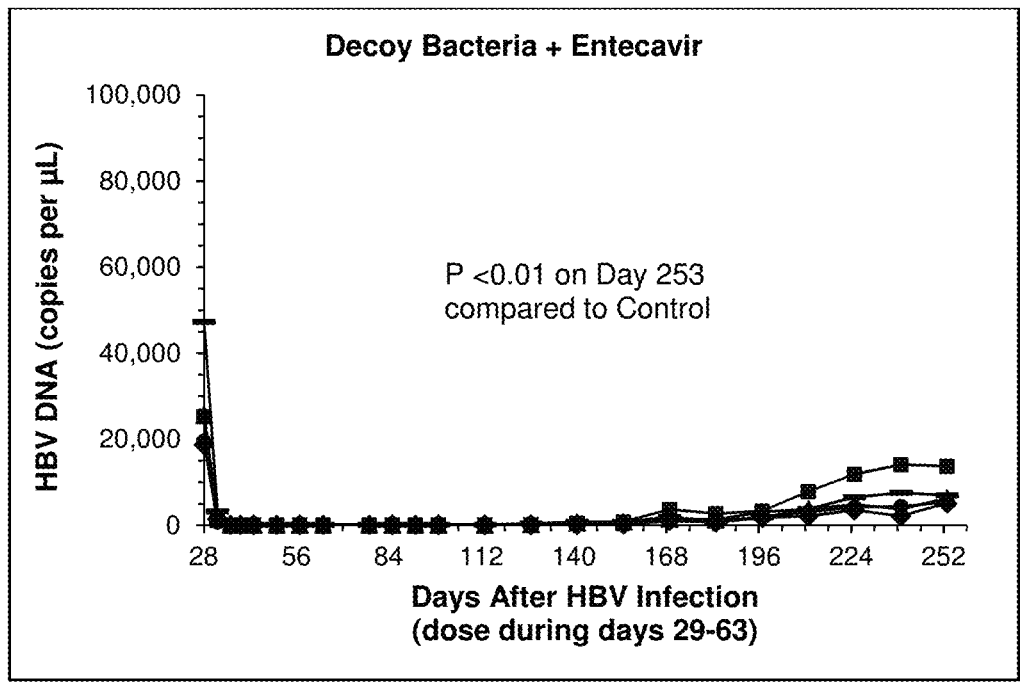

FIG. 3A demonstrates that indomethacin alone did not inhibit HBV DNA production. Whereas, FIG. 3 (B, C and D) demonstrates that ETV, Decoy or ETV+Decoy inhibited HBV DNA production, in the presence of indomethacin, in a similar fashion to that observed in the absence of indomethacin (FIG. 1). No body weight loss was observed with ETV treatment. Transient body weight loss of 6% for one day was observed during the 1$^{st}$ week of Decoy treatment (±ETV), 1.3% (no ETV) and 3.4% (+ETV) for one day during the 2$^{nd}$ week of Decoy treatment, 0.8% (no ETV) and 2.0% (+ETV) for one day during the third week of treatment and no body weight loss was observed during the fourth and fifth weeks of Decoy treatment (±ETV).

Statistically significant inhibition of HBV DNA was lost at termination (day 253), 27 weeks after cessation of ETV treatment (FIG. 3B), but inhibition remained statistically significant at day 253 in the Decoy (FIG. 3C) and Decoy+ETV (FIG. 3D) groups. This demonstrates that Decoy has a longer lasting inhibitory effect than ETV.

Figure 4A:
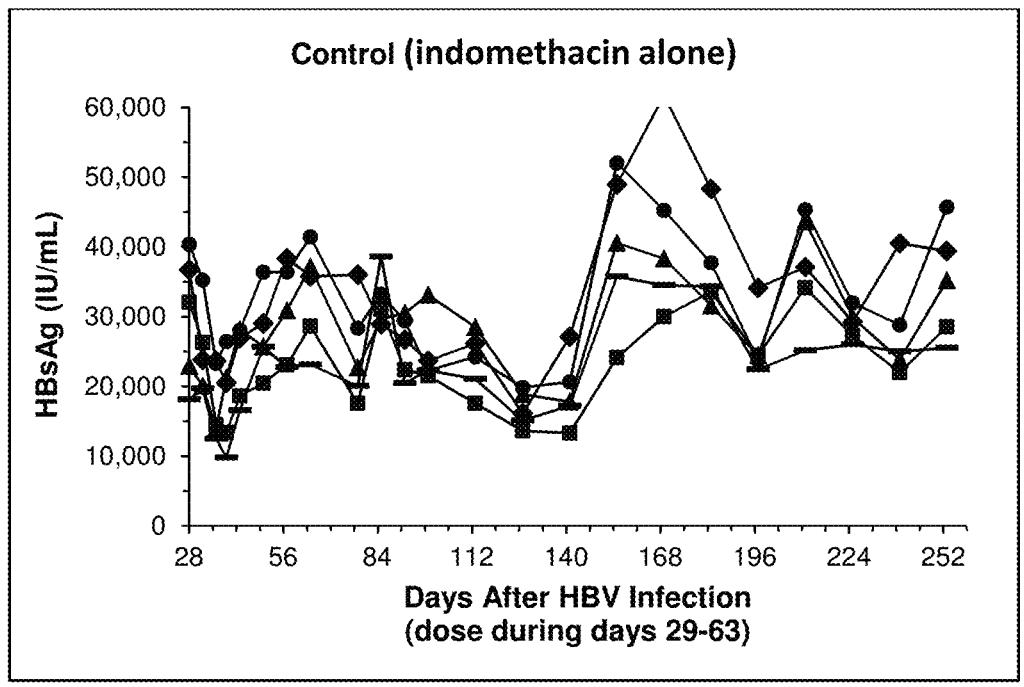
FIG. 4A-D present the results of inhibition of HBsAg expression in vivo.
Figure 4B:
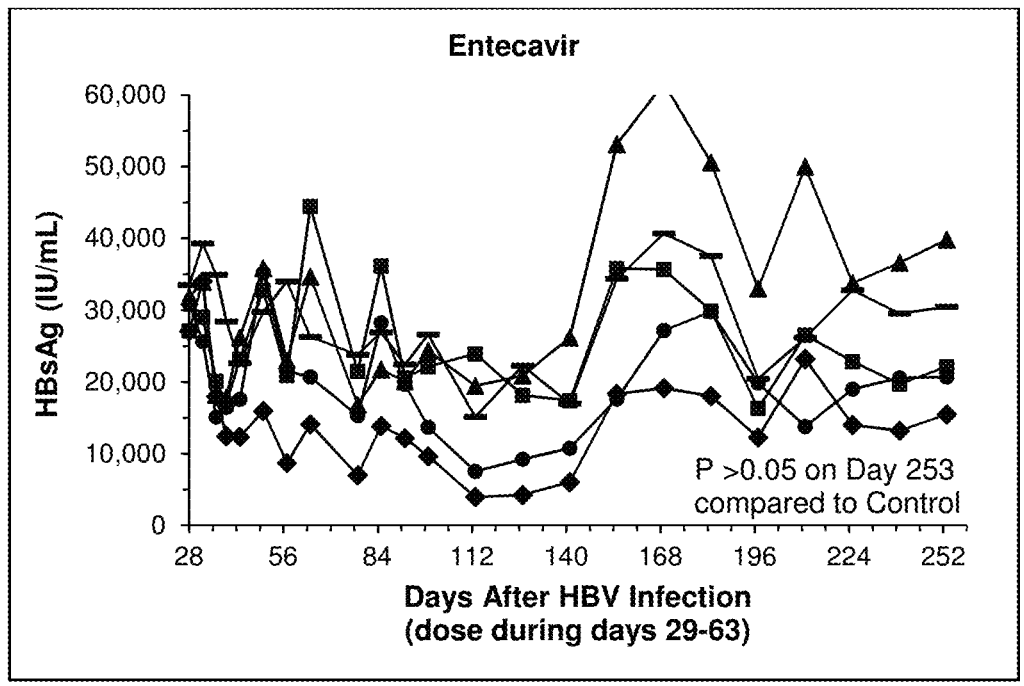
Figure 4C:
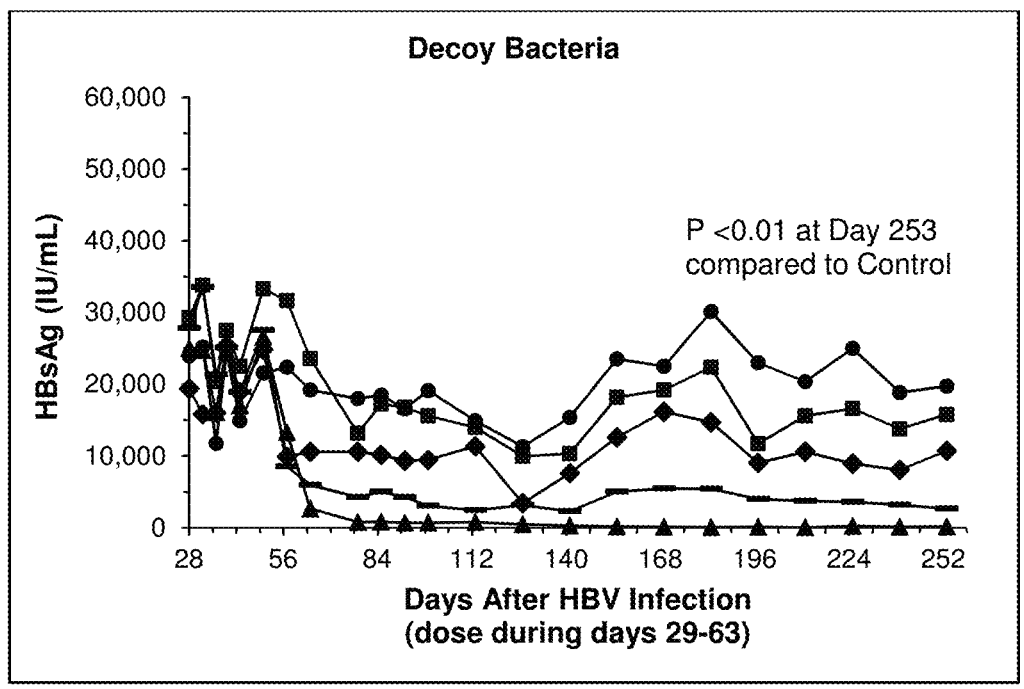
Figure 4D:
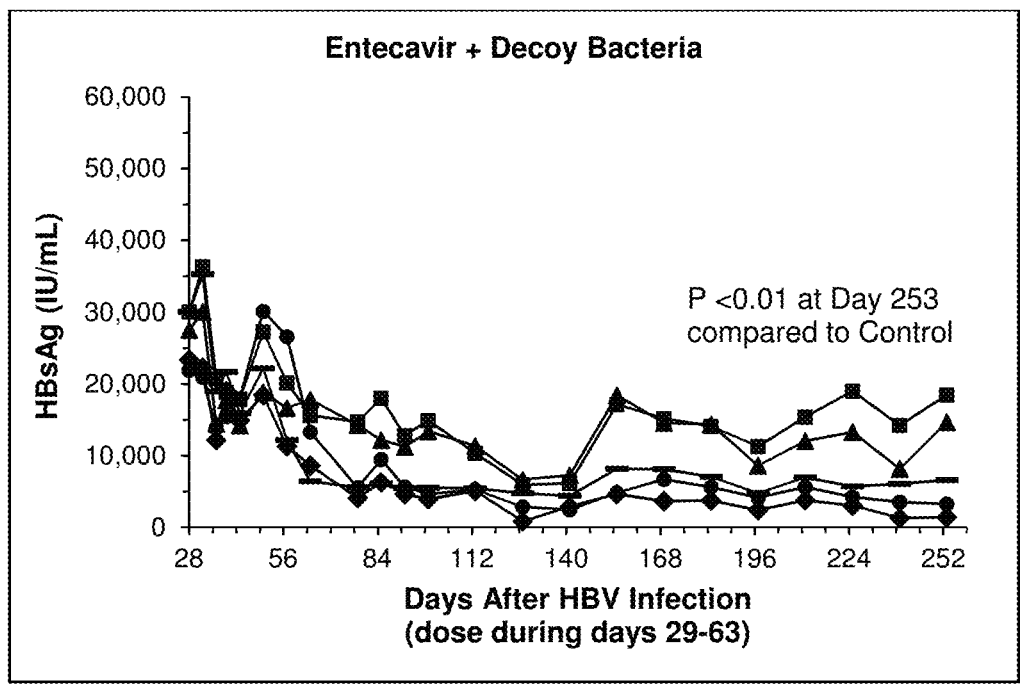
Figure 5A:
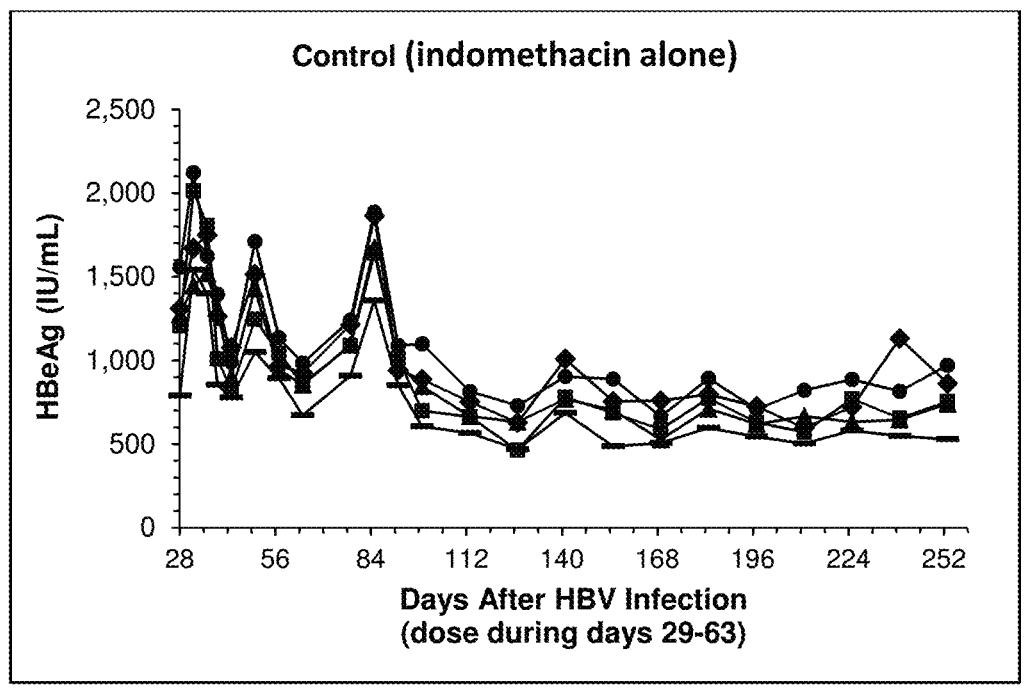
FIG. 5A-D present the results of inhibition of HBeAg expression in vivo.
Figure 5B:
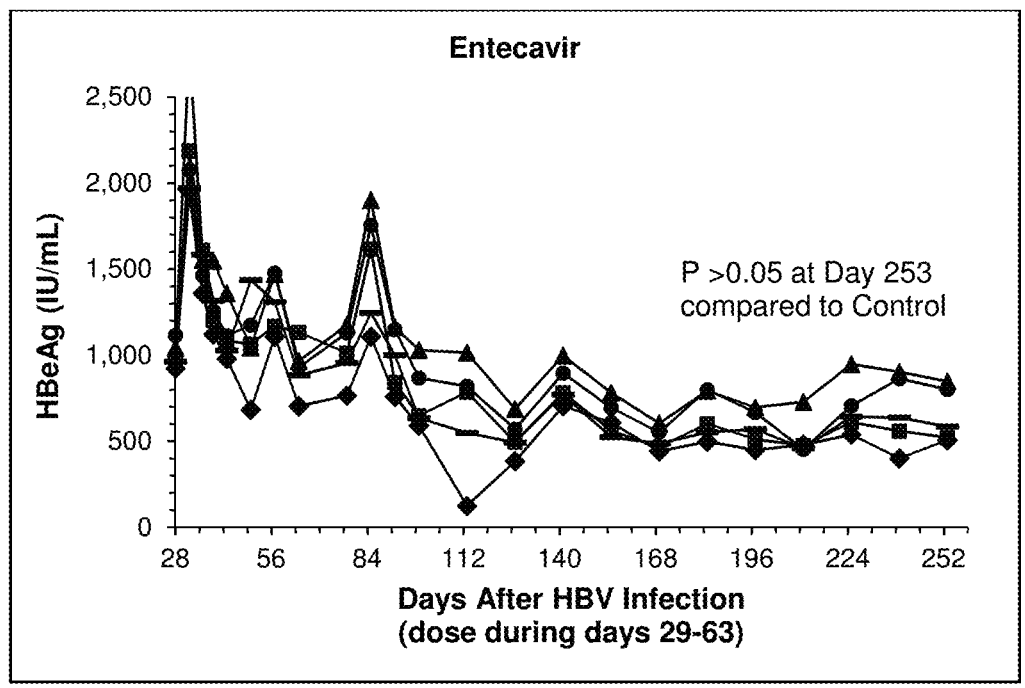
Figure 5C:
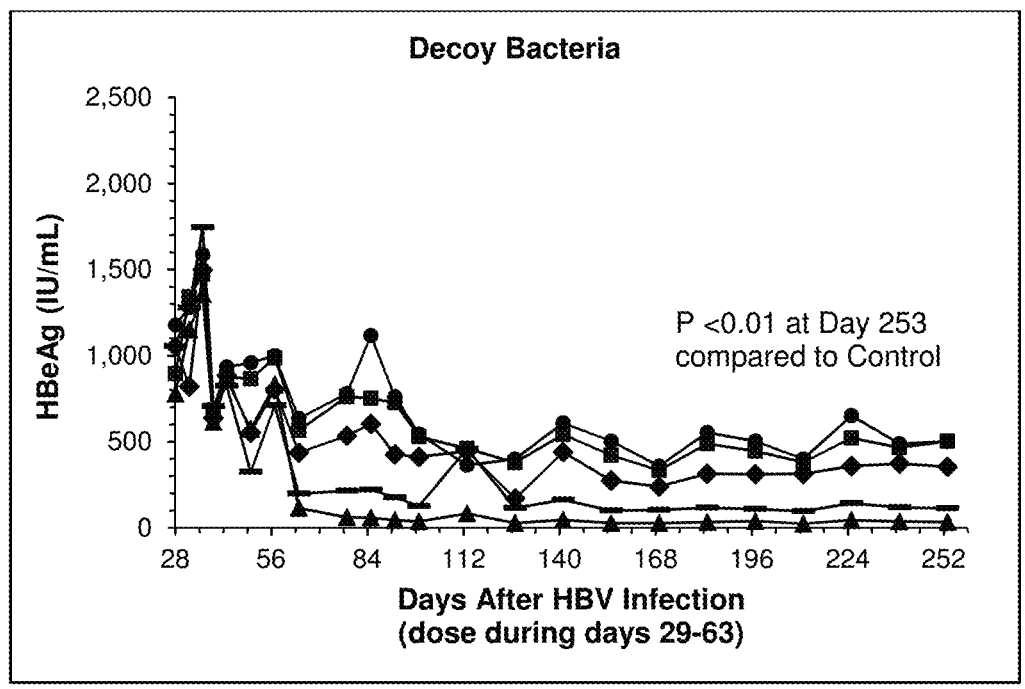
Figure 5D:
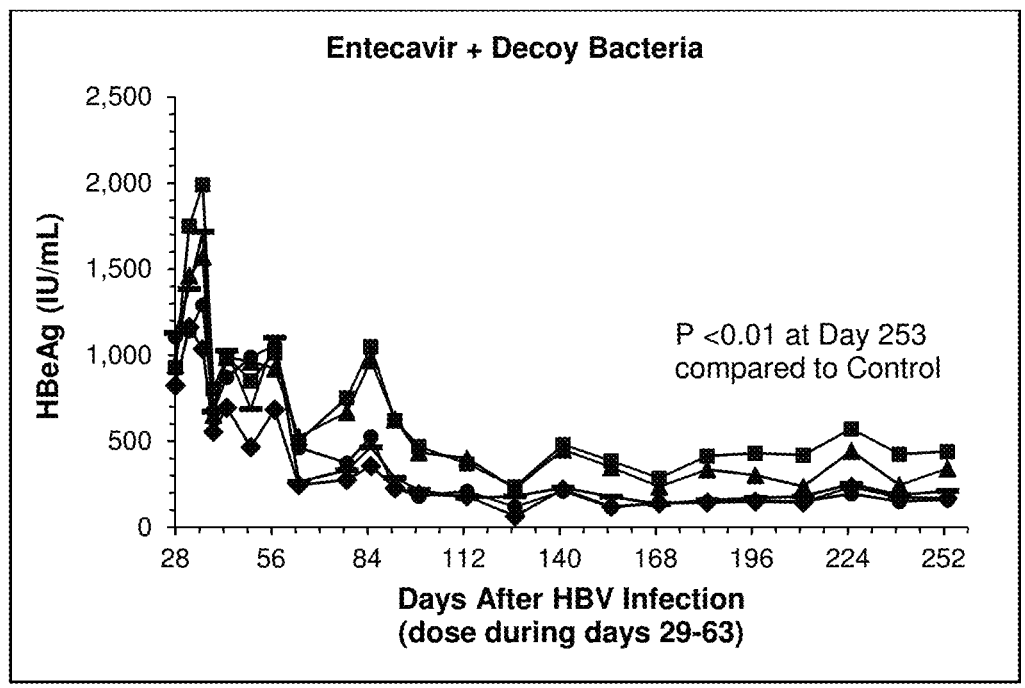

Indomethacin+ETV did not inhibit HBsAg or HBeAg relative to indomethacin alone (FIGS. 4A, B and 5 A, B). However, the addition of Decoy (i.e., indomethacin+Decoy or indomethacin+Decoy+ETV) inhibited HBsAg and HBeAg production relative to indomethacin alone (FIGS. 4A, C, D and 5 A C, D). Since neither Decoy alone, nor indomethacin alone inhibited HBsAg production, these results demonstrate that there is a synergistic interaction between Decoy and indomethacin, with respect to inhibition of HBsAg.

Figure 6:
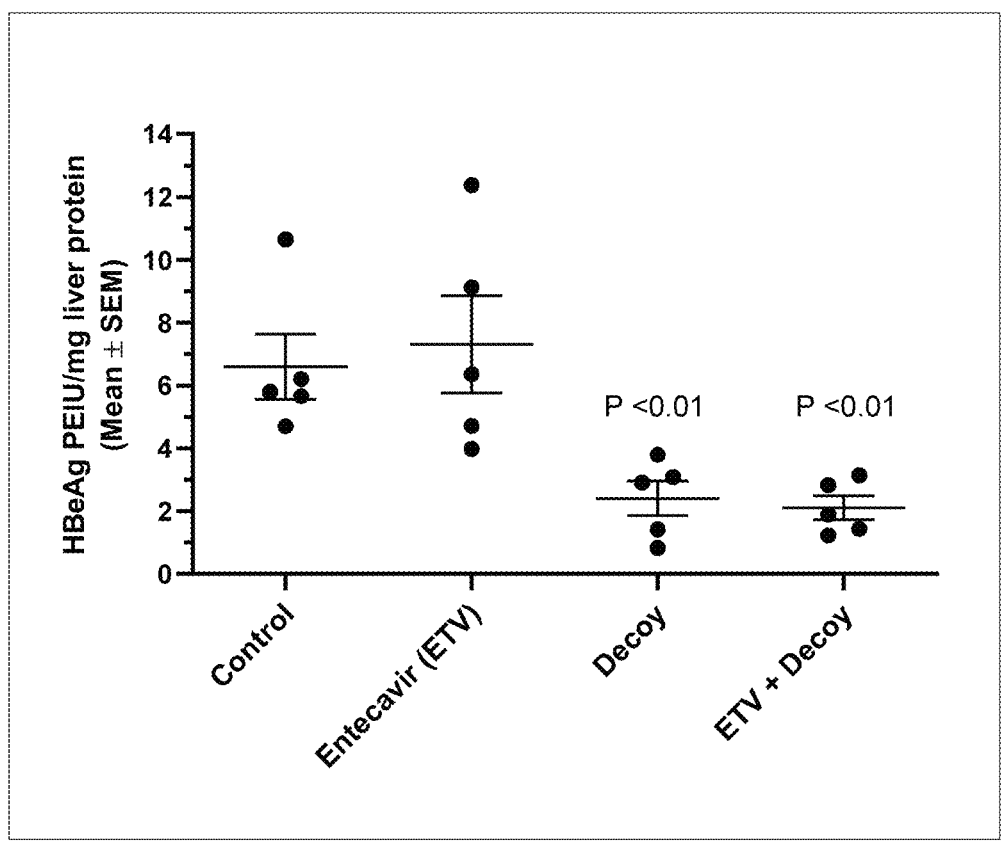
FIG. 6 shows that the combination of indomethacin and Decoy bacteria (with or without Entecavir) inhibited HBeAg expression in mouse livers 27 weeks after the cessation of treatment.
Figure 7A:
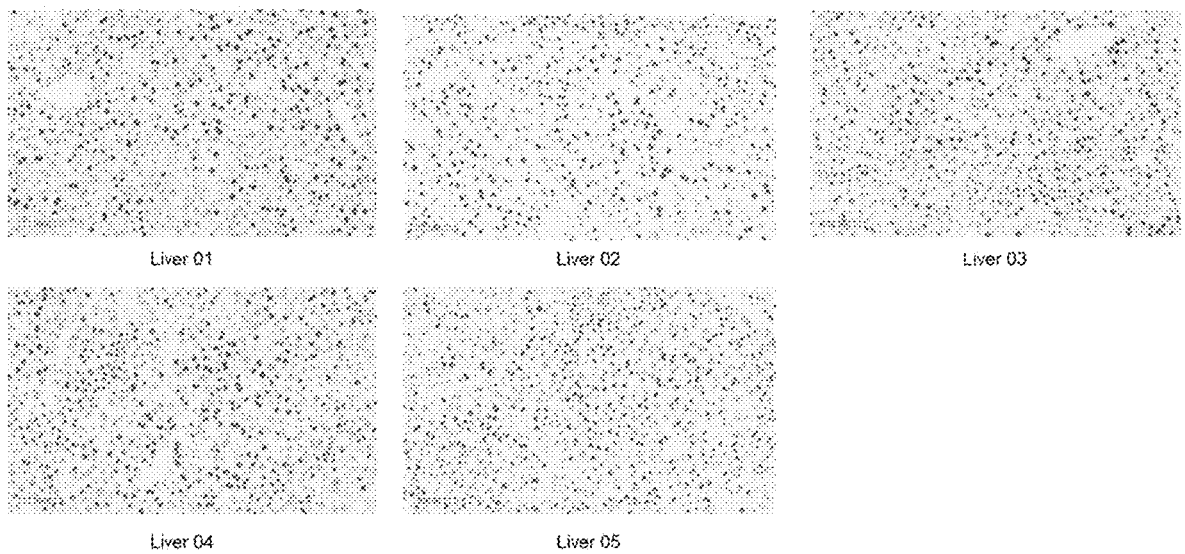
FIG. 7A-F present immunohistochemical analysis of HBcAg expression in mouse livers 27 weeks after the cessation of treatment.
Figure 7B:
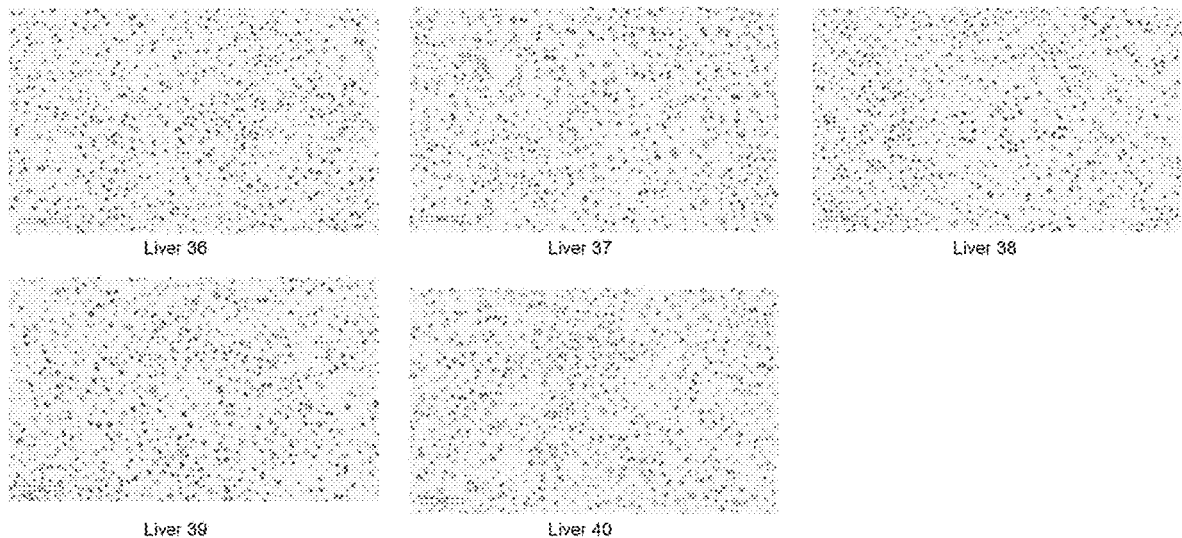
Figure 7C:
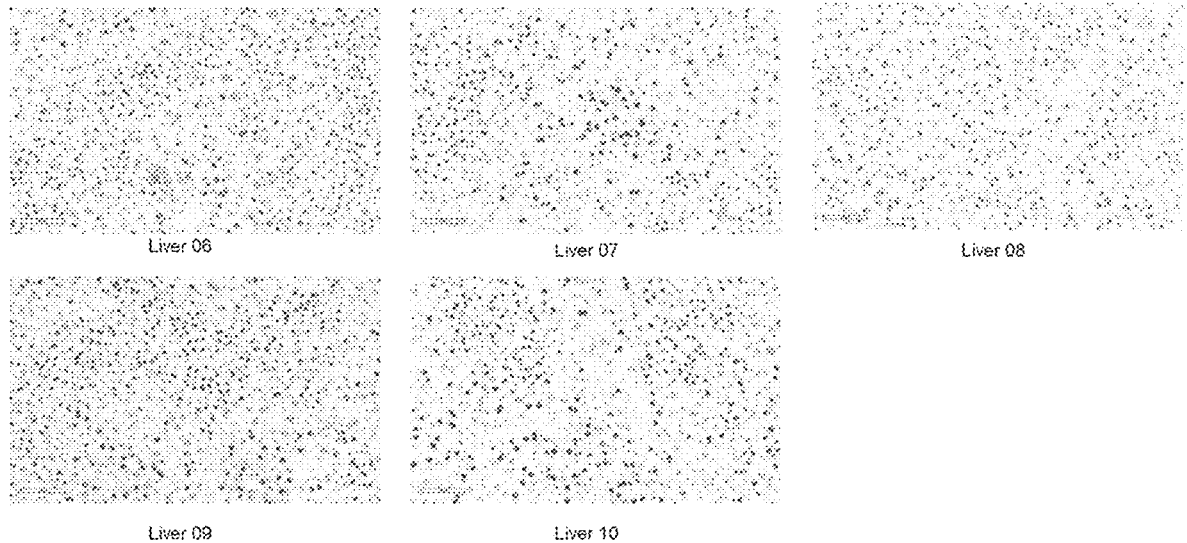
Figure 7D:
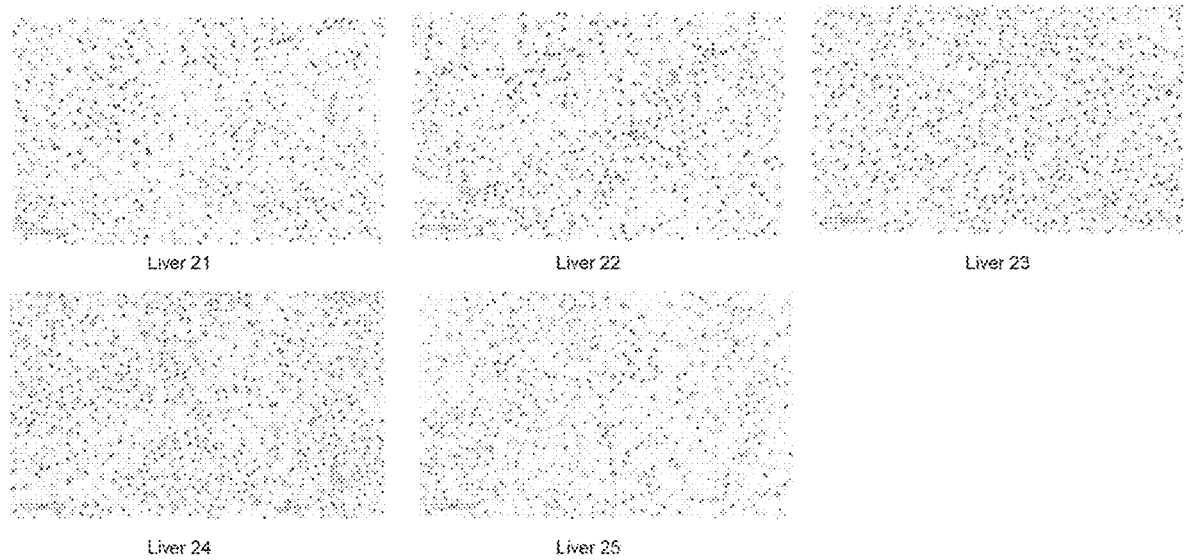
Figure 7E:
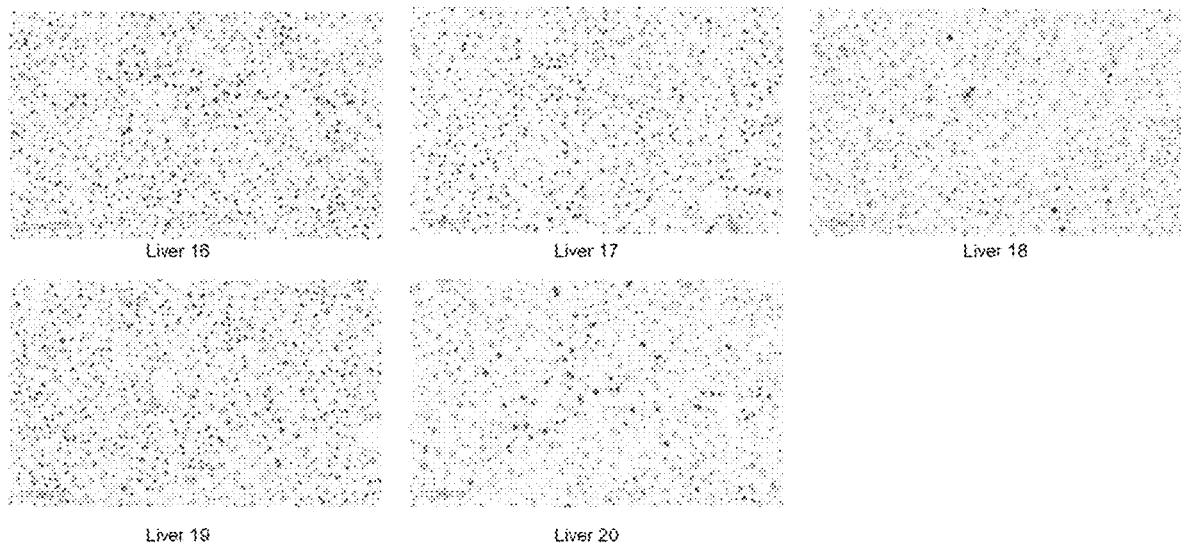
Figure 7F:
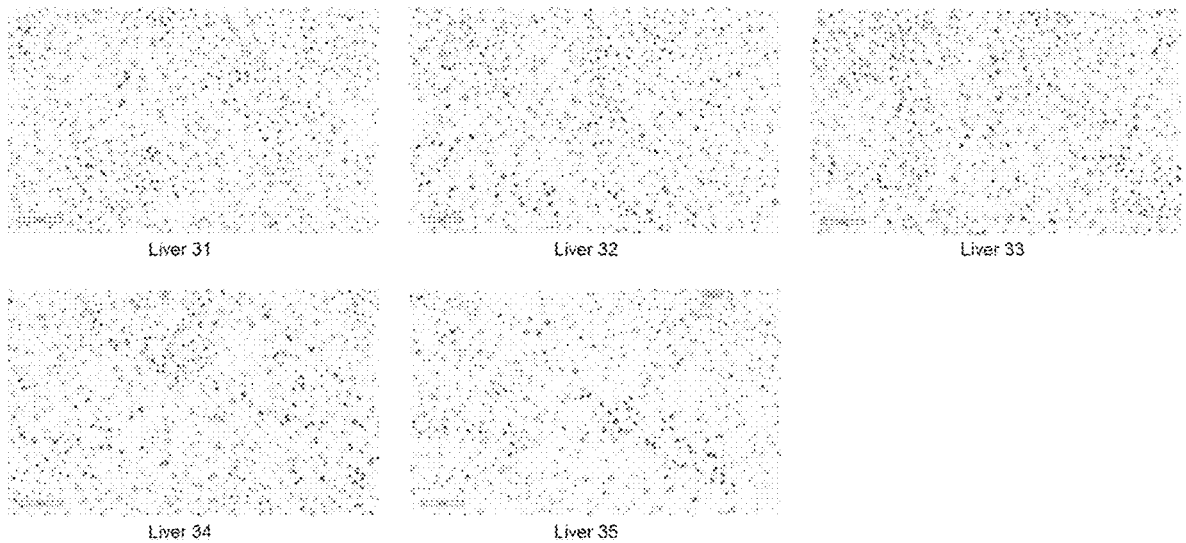

FIG. 6 demonstrates that in the presence of indomethacin, Decoy or Decoy+ETV, but not ETV, inhibited HBeAg expression in the livers of mice 27 weeks after the cessation of treatment. FIG. 7 represents IHC analysis of HBcAg expression in livers of Decoy vehicle (i.e., buffer only used in the Decoy composition) and compound treated mice. The combination of indomethacin and Decoy, again, reduced HBcAg expression in 2 out of 5 mice, relative to indomethacin alone, and the combination of indomethacin, Decoy and ETV reduced the expression of HBcAg in 5 out of 5 mice relative to treatment with indomethacin+ETV or indomethacin+Decoy.

This example demonstrates that NSAIDs, such as indomethacin, are not capable of inhibiting HBV, but can significantly enhance the antiviral activity of Decoy bacteria in a synergistic manner. Compared to the standard of care, ETV, Decoy bacteria exhibited longer and more sustained treatment effects. The combination of Decoy and ETV resulted in significant improvement over each treatment alone as well, in particular, with respect to long-term observation after cessation of treatment.

Example 6. Inhibition of HIV Infection

In order to examine the potential of Decoy bacteria to inhibit human immunodeficiency virus (HIV) infection in vivo, a human immune system was reconstituted in NOD/Shi-scid/IL-2Rγnull-specific (NCG) immunodeficient female mice (Charles River) with hematopoietic stem cells isolated from human cord blood. Mice were engrafted with cord blood-derived CD34+ hematopoietic stem and progenitor cells (French Blood Institute) after chemical myeloablative treatment (Manfroi et al., Can. Res. v77, pp1097-1107 2017). Engraftment consisted of intravenous injection of 105CD34+ cells. Engraftment level was monitored by the analysis of human CD45+ cells among total blood leukocytes by flow cytometry.

After 14 weeks of engraftment, qualified hu-mice were inoculated with 80 ng of HIV-1 (NL4-3 HIV1/Clade B; X4 tropism virus) by i.p. injection. Plasma viremia was determined at week 5 by qRT-PCR. Other methods were as described in Wenzel et al., J. Virol.

Doi: 10.1128/JVI.00907-19 (accepted manuscript posted online 2 Aug. 2019). Only HIV-mice with a viral load above $10^4$ copies/mL were used in the experiment. At week 5, mice were randomized into groups based on their humanization rate, HIV load and percentage of CD4+ T cells in blood.

Groups were treated with Decoy vehicle i.v., twice per week for 5 weeks, highly active anti-retroviral therapy (HAART or tri-therapy), consisting of 2.4 mg of Lamivudine, 2.35 mg of Tenofovir Disproxil and 19.2 mg of Raltegravir per day in food pellets for 6 weeks, or Decoy killed bacteria (prepared as described in Example 4) $6×10^7$ i.v. (tail vein) twice per week for 5 weeks.

Blood (100 µL) was collected every two weeks from the retro-orbital sinus in EDTA-coated tubes. Plasma was separated from cells by centrifugation and was incubated 30 min at 56° C. to inactivate HIV prior to freezing at −80° C. Viral RNAs were extracted from 40 μL of frozen inactivated plasma using an automated nucleic acid purification device (Arrow, NorDiag) and Viral RNA Extraction Kit (DiaSorin, #12-08-02). HIV plasma viral load was determined by qRT-PCR using the "Generic HIV Charge Virale" kit (Biocentric, #TR001-440IC, Batch 0089/08A). The limit of sensitivity was set as 1000 copies/mL. Values below this threshold were considered as undetected. Inhibitory activity was determined by comparing treated groups at each time point to the vehicle group at the same time-point by unpaired, non-parametric Mann-Whitney statistical analysis. Asterisk symbols denote statistically significant inhibition.

Figure 8A:
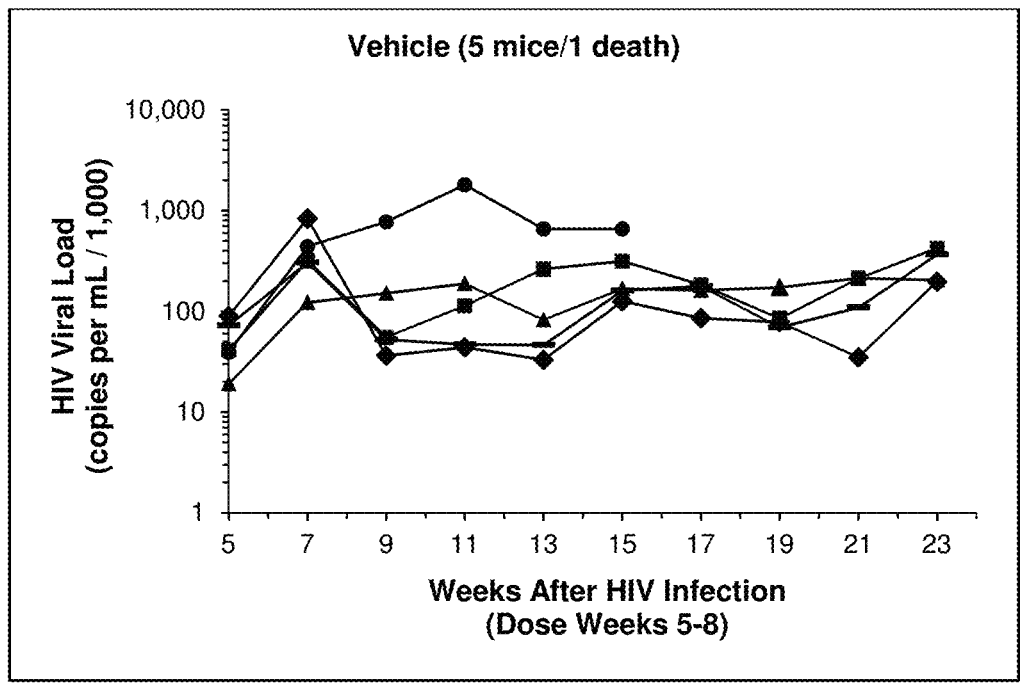
FIG. 8A-C show the inhibition of HIV blood levels by standard of care treatment or treated bacteria in humanized mice infected with HIV.
Figure 8B:
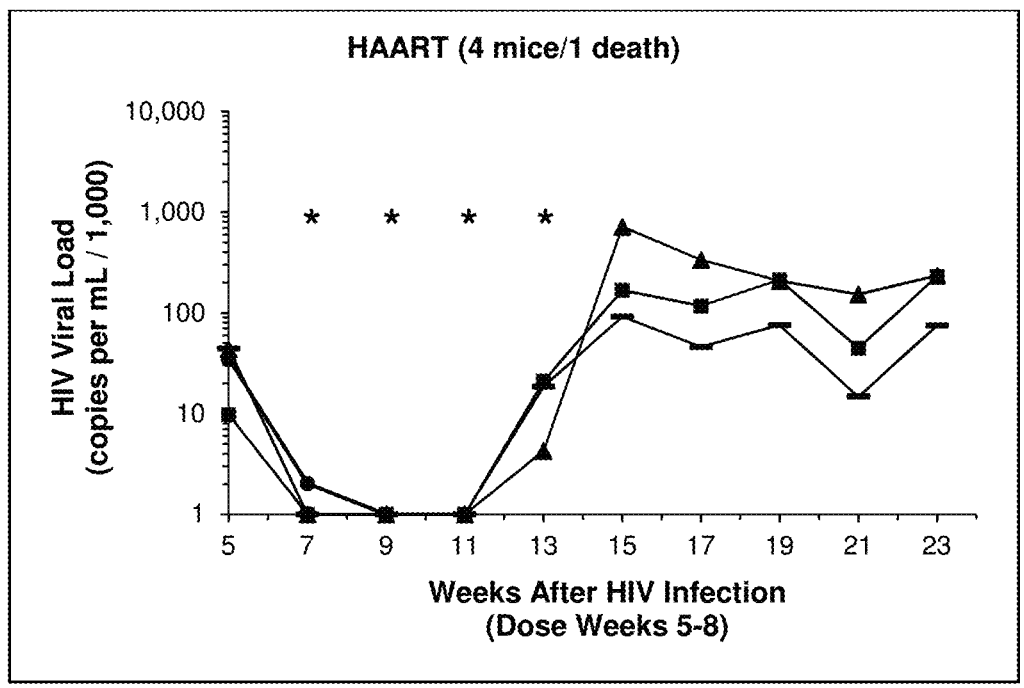
Figure 8C:
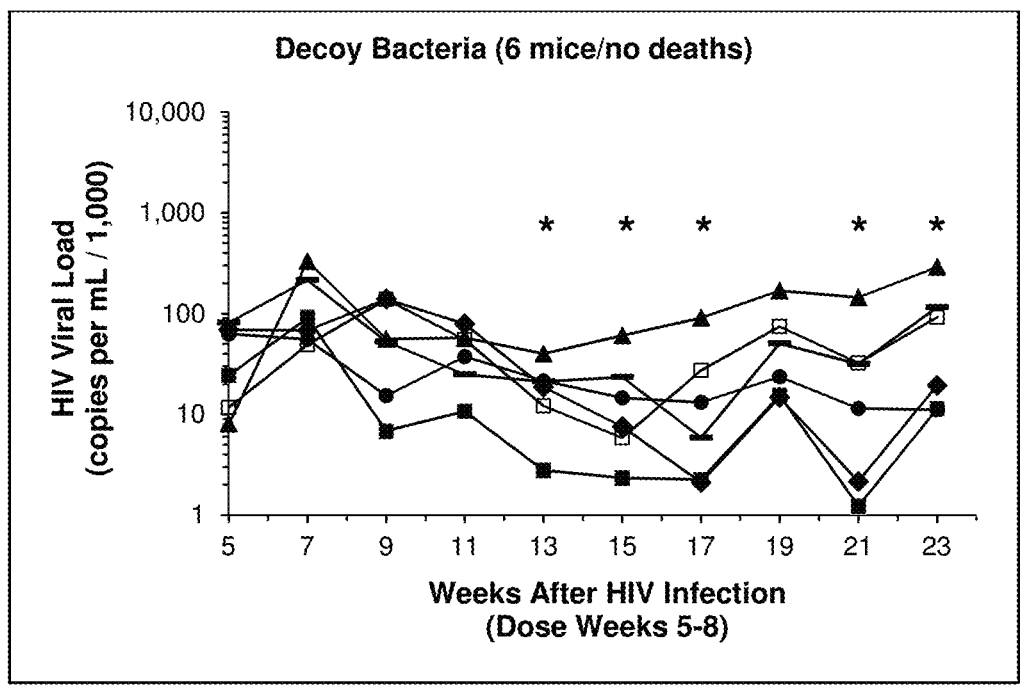

FIG. 8 demonstrates that HAART therapy inhibited HIV blood levels two weeks after starting treatment and continuing for three weeks after cessation of treatment (FIG. 8B). Decoy bacteria did not inhibit HIV levels during treatment, but inhibition was observed starting four weeks after cessation of treatment, lasting for eleven weeks, with the exception of week 19 (FIG. 8C). The delayed inhibitory response suggests that Decoy bacteria were able to induce an immune response against the HIV infection. One mouse death each was recorded in the Decoy vehicle group and the group treated with HAART. No deaths were observed in the Decoy-treated group.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method of preventing or treating an infection in a patient in need thereof, comprising administering to the patient an effective amount of a composition comprising a plurality of intact and substantially non-viable Gram-negative bacterial cells which have been treated in such a way as to result in about 75% to 99% reduction of lipopolysaccharide (LPS)-associated endotoxin activity when measured by the Limulus Amebocyte Lysate (LAL) assay as compared to untreated, wild-type Gram-negative bacterial cells, wherein the infection is by an influenza A virus, an influenza B virus or an influenza C virus.

2. The method of claim 1, wherein the composition contains about 0.01 to 100 ng active LPS per kg body weight of the patient.

3. The method of claim 1, wherein the composition contains about 2 to 200 ng active LPS per $1\times10^8$ cells.

4. The method of claim 1, wherein the intact and substantially non-viable Gram-negative bacterial cells have been treated in such a way as to result in about 85% to 98% reduction of LPS-associated endotoxin.

5. The method of claim 1, wherein the administration starts within 24 hours following the infection, or within 2 days, 3 days, 4 days, 5 days, 6 days or 7 days following the infection.

6. The method of claim 1, wherein the administration starts after at least 24 hours following the infection, or after at least 2 days, 3 days, 4 days, 5 days, 6 days or 7 days following the infection.

7. The method of claim 1, wherein at least 90%, 95% or 100% of the bacterial cells are non-viable.

8. The method of claim 1, wherein the bacterial cells are *Salmonella* or *Escherichia* cells.

* * * * *